(12) United States Patent
Heyman et al.

(10) Patent No.: US 7,078,501 B2
(45) Date of Patent: Jul. 18, 2006

(54) TOPOISOMERASE LINKER-MEDIATED AMPLIFICATION METHODS

(75) Inventors: John A. Heyman, Rixensart (BE); Gabor Szalai, West Columbia, SC (US); Michael Felder, Columbia, SC (US); Knut R. Madden, Carlsbad, CA (US)

(73) Assignees: Invitrogen Corporation, Carlsbad, CA (US); South Carolina Research Institute, Columbia, SC (US)

( * ) Notice: Subject to any disclaimer, the term of this patent is extended or adjusted under 35 U.S.C. 154(b) by 190 days.

(21) Appl. No.: 09/792,875

(22) Filed: Feb. 23, 2001

(65) Prior Publication Data

US 2001/0044137 A1 Nov. 22, 2001

Related U.S. Application Data

(60) Provisional application No. 60/184,858, filed on Feb. 25, 2000.

(51) Int. Cl.
C07H 21/04 (2006.01)
C12Q 1/68 (2006.01)
C12P 19/34 (2006.01)

(52) U.S. Cl. ............... 536/23.1; 536/23.2; 536/23.5; 536/24.1; 536/24.3; 536/24.23; 435/6; 435/91.1; 435/91.2

(58) Field of Classification Search ............... 536/23.1, 536/23.2, 23.5, 24.1, 24.31, 24.33; 435/91.1, 435/91.2, 6
See application file for complete search history.

(56) References Cited

U.S. PATENT DOCUMENTS

| | | | |
|---|---|---|---|
| 4,661,450 A | 4/1987 | Kempe | 435/172.3 |
| 4,800,159 A | 1/1989 | Mullis | 435/172.3 |
| 5,162,209 A | 11/1992 | Scheele | 435/91 |
| 5,624,826 A | 4/1997 | Kato et al. | 435/91.4 |
| 5,746,997 A | 5/1998 | Reed | 424/1.73 |
| 5,766,891 A | 6/1998 | Shuman | 435/91.41 |
| 5,851,808 A | 12/1998 | Elledge et al. | 435/172.3 |
| 5,958,681 A | 9/1999 | Wetmur et al. | 435/6 |
| 5,981,182 A | 11/1999 | Jacobs, Jr. et al. | 435/6 |

(Continued)

FOREIGN PATENT DOCUMENTS

| | | |
|---|---|---|
| EP | 0 373 914 A2 | 12/1989 |
| EP | 0 625 572 A1 | 9/1993 |
| EP | 1 018 549 A1 | 7/2000 |

(Continued)

OTHER PUBLICATIONS (J. of Biol. Chem. (1997) 272(42): 26441–47).*
Sigma Catalog (1996).*
Carninci, et al. "High–Efficiency Full–Length cDNA Cloning by Biotinylated CAP Trapper," *Genomics*, 37(3):327–36 (1996) Academic Press, Inc.

(Continued)

Primary Examiner—Jezia Riley
(74) Attorney, Agent, or Firm—DLA Piper Rudnick Gray Cary US LLP

(57) ABSTRACT

A Vaccinia topoisomerase-adapted linker, which contains an oligonucleotide primer binding site of known sequence, useful for specifically joining the linker to the end of a polynucleotide of unknown sequence and allowing subsequent PCR amplification of the polynucleotide or DNA is provided. Kits containing the invention Vaccinia topoisomerase-adapted linker and one or more linker-specific oligonucleotides for annealing to the linker in PCR are also provided. In addition, the invention provides methods for using the invention linkers in linker-mediated PCR amplification procedures for isolation and optional sequencing of isolated PCR amplification products.

2 Claims, 1 Drawing Sheet

U.S. PATENT DOCUMENTS

| | | | | |
|---|---|---|---|---|
| 6,013,440 | A | * 1/2000 | Lipshutz et al. | 435/6 |
| 6,140,086 | A | 10/2000 | Fox et al. | |
| 6,174,669 | B1 | 1/2001 | Hayashizaki et al. | 435/6 |
| 6,238,884 | B1 | 5/2001 | Short | 435/69.1 |
| 6,277,632 | B1 | 8/2001 | Harney | |
| 6,280,977 | B1 | 8/2001 | Liang | 435/91.2 |
| 6,291,213 | B1 | 9/2001 | Rothstein | 435/91.2 |
| 6,340,595 | B1 | 1/2002 | Vogels et al. | |
| 6,537,776 | B1 | 3/2003 | Short | |
| 6,548,277 | B1 | 4/2003 | Shuman | |
| 6,653,106 | B1 | * 11/2003 | Shuman et al. | 435/91.1 |
| 2002/0025561 | A1 | 2/2002 | Hodgson | |
| 2002/0028444 | A1 | 3/2002 | Harney et al. | |
| 2002/0068290 | A1 | 6/2002 | Yarovinsky | 435/6 |
| 2002/0182731 | A1 | 12/2002 | Ji et al. | |

FOREIGN PATENT DOCUMENTS

| | | |
|---|---|---|
| WO | 85/04898 | 11/1985 |
| WO | 94/29443 | 12/1994 |
| WO | 96/19497 | 6/1996 |
| WO | 96/34981 | 11/1996 |
| WO | 97/24455 | 7/1997 |
| WO | WO 97/48716 | 12/1997 |
| WO | 98/20122 | 5/1998 |
| WO | 98/55502 | 12/1998 |
| WO | 98/56943 | 12/1998 |
| WO | WO 00/12687 | 3/2000 |
| WO | 00/56878 | 9/2000 |
| WO | 01/62892 A2 | 8/2001 |
| WO | WO 02/16594 | 2/2002 |
| WO | 02/061034 A2 | 8/2002 |

OTHER PUBLICATIONS

Carninci, et al. "High Efficiency Selection of full–length cDNA by Improved Biotinylated Cap Trapper," *DNA Research*, 4:61–66 (1997). Universal Academy Press.

Cheng and Shuman, "DNA strand transfer catalyzed by vaccinia topoisomerase: ligation of DNAs containing a 3'mononucleotide overhang," *Nucleic Acids Res.*, 28(9):1893–8. (2000). Oxford University Press.

Cheng and Shuman, "Recombinogenic flap ligation pathway for intrinsic repair of topoisomerase IB–induced double–strand breaks," *Mol. Cell. Biol.* 20(21):8059–8068 (2000) American Society for Microbiology.

Cheng and Shuman, "Site–specific DNA transesterification by vaccinia topoisomerase: Role of specific phosphates and nucleosides," *Biochemistry* 38(50):16599–612 (1999) American Chemical Society.

Cheng and Shuman, "A catalytic domain of eukaryotic DNA topoisomerase I," *J. Biol. Chem.* 273(19):11589–95 (1998) The American Society for Biochemistry and Molecular Biology, Inc.

Cheng, et al., "Conservation of structure and mechanism between eukaryotic topoisomerase I and site–specific recombinases," *Cell*. 92(6):841–50 (1998) Cell Press.

Cheng, et al., "Mutational analysis of 39 residues of vaccinia DNA topoisomerase identifies Lys–220, Arg–223, and Asn–228 as important for covalent catalysis," *J. Biol. Chem*. 272(13):8263–9 (1997) The American society for Biochemistry and Molecular Biology, Inc.

DiGate and Marians, "Molecular Cloning and DNA Sequence Analysis of *Escherichia Coli topB*, the Gene Encoding Topoisomerase III," *J. Biol. Chem*. 264(30):17924–17930 (1989). The American society for Biochemistry and Molecular Biology, Inc.

Edery, et al., "An Efficient Strategy to Isolate Full–Length cDNAs Based on an mRNA Cap Retention Procedure (CAPture)," *Mol Cell. Biol*., 15(6):3363–3371 (1995). American Society for Microbiology.

Ericsson, et al., "Characterization of ts 16, a temperature–sensitive mutant of vaccinia virus," *J. Virol*.. 69(11):7072–86 (1995) American Society for Microbiology.

Gross and Shuman, "Vaccinia virions lacking the RNA helicase nucleoside triphosphate phosphohydrolase II are defective in early transcription," *J. Virol*. 70(12):8549–5 (1996) American Society for Microbiology.

Haghighat and Sonenberg. "eIF4G Dramatically Enhances the Binding of eIF4E to the mRNA 5'–Cap Structure," *J. Biol. Chem*., 272(35):21677–21680 (1997). The American society for Biochemistry and Molecular Biology, Inc.

Haghighat et al., "The eIF4G–eIF4E Complex is the Target for Direct Cleavage by the Rhinovirus 2A Proteinase," *J. Virol*. 70:8444–8450 (1996). American Society for Microbiology.

Henningfeld and Hecht, "A model for topoisomerase I–mediated insertions and deletions with duplex DNA substrates containing branches, nicks, and gaps," *Biochemistry* 34(18):6120–9. (1995) American Chemical Society.

Invitrogen Corporation. *Invitrogen Catalog*, Carlsbad, California, pp. 18, 29, 43, 44, 49–52 (1998).

Janknecht, et al., "Rapid and efficient purification of native histidine–tagged protein expressed by recombinant vaccinia virus," *Proc. Natl. Acad. Sci., U S A* 88:8972–8976(1991) National Academic of Sciences.

Kane and Shuman, "Vaccinia virus morphogenesis is blocked by a temperature–sensitive mutation in the I7 gene that encodes a virion component," *J. Virol*. 67(5):2689–98 (1993) American Society for Microbiology.

Kato, et al., "Construction of a Human Full–Length cDNA Bank," *Gene*. 150: 243–250 (1994) Elsevier Science.

Klemm, et al., "Peptide inhibitors of DNA cleavage by tyrosine recombinases and topoisomerases," *J. Mol. Biol*. 299(5):1203–16. (2000) Academic Press, Inc.

Klemperer, et al., "Identification and characterization of the orf virus type I topoisomerase," *Virology* 206:203–215 (1995) Academic Press, Inc.

Krogh and Shuman, "Vaccinia topoisomerase mutants illuminate conformational changes during closure of the protein clamp and assembly of a functional active site," *J. Biol. Chem*. Jul. 5, 2001 [Manuscript]The American Society for Biochemistry and Molecular Biology, Inc.

Krogh and Shuman, "Catalytic mechanism of DNA topoisomerase IB," *Mol. Cell*.. 5(6):1035–41 (2000) Cell Press.

Krogh and Shuman, "DNA strand transfer catalyzed by vaccinia topoisomerase: peroxidolysis and hydroxylaminolysis of the covalent protein–DNA intermediate," *Biochemistry* 39(21):6422–32. (2000) American Chemical Society.

Krogh, et al., "Effect of 2'–5'phosphodiesters on DNA transesterification by vaccinia topoisomerase," *J. Biol. Chem*. 276(24):20907–20912. (2001) The American Society for Biochemistry and Molecular Biology, Inc.

Krogh, et al., Melanoplus sanguinipes entomopoxvirus DNA topoisomerase: site–specific DNA transesterification and effects of 5'–bridging phosphorothiolates, *Virology* 264(2):441–51. (1999) Academic Press, Inc.

Maruyama and Sugano, "Oligo–Capping: A Simple Method to Replace the Cap Structure of Eukaryotic mRNAs with Oligoribonucleotides," *Gene*. 138:171–174 (1994).

Morham and Shuman, "Covalent and Noncovalent DNA Binding by Mutants of Vaccinia DNA Topoisomerase I," *J. Biol. Chem.* 267:15984–15992 (1992) The American Society for Biochemistry and Molecular Biology, Inc.

Morham and Shuman, "Phenotypic selection and characterization of mutant alleles of a eukaryotic DNA topoisomerase I," *Genes. Dev.* 4(4):515–24 (1990) Cold Spring Harbor Laboratory Press.

Palaniyar, et al. "SFV topoisomerase: sequence specificity in a genetically mapped interval," *Virology* 221:351–354 (1996). American Press, Inc.

Petersen and Shuman, "DNA strand transfer reactions catalyzed by vaccinia topoisomerase: hydrolysis and glycerololysis of the covalent protein–DNA intermediate," *Nucleic Acids Res.* 25(11):2091–7 (1997) Oxford University Press.

Petersen and Shuman, "Histidine 265 is important for covalent catalysis by vaccinia topoisomerase and is conserved in all eukaryotic type I enzymes," *J. Biol. Chem.* 272(7):3891–6 (1997) The American Society for Biochemistry and Molecular Biology, Inc.

Petersen et al., "Characterization of a DNA topoisomerase encoded by Amsacta moore entomopoxvirus," *Virology* 230(2):197–206 (1997) Academic Press, Inc.

Petersen, et al., "Mutations within a conserved region of vaccinia topoisomerase affect the DNA cleavage–religation-–equilibrium," *J. Mol. Biol.* 1263(2):181–95 (1996) Academic Press Limited.

Salazar et al., "The DNA strand in DNA.RNA hybrid duplexes is neither B–form nor A–form in solution," *Biochemistry* 32(16):4207–15 (1993) American Chemical Society.

Schmitt, et al., "Affinity purification of histidine–tagged proteins," *Molecular Biology Reports* 18:223–230 (1993).

Sekiguchi and Shuman, "Domain structure of vaccinia DNA ligase," *Nucleic Acids Res.* 25(4):727–34 (1997) Kluwer Academic Publishers.

Sekiguchi and Shuman, "Mutational analysis of vaccinia virus topoisomerase identifies residues involved in DNA binding," *Nucleic Acids Res.* 25(18):3649–56. (1997) Oxford University Press.

Sekiguchi and Shuman, "Nick sensing by vaccinia virus DNA ligase requires a 5'phosphate at the nick and occupancy of the adenylate binding site on the enzyme," *J. Virol.* 71(12):9679–84 (1997) American Society for Microbiology.

Sekiguchi and Shuman, "Site–specific ribonuclease activity of eukaryotic DNA topoisomerase I," *Mol. Cell.* 1(1):89–97.(1997) Cell Press.

Sekiguchi and Shuman, "Covalent DNA binding by vaccinia topoisomerase results in unpairing of the thymine base 5'of the scissile bond," *J. Biol. Chem.* 271(32):19436–42 (1996). The American Society for Biochemistry and Molecular Biology, Inc.

Sekiguchi and Shuman, "Identification of contacts between topoisomerase I and its target DNA by site–specific photo-crosslinking," *EMBO J.* 15(13):3448–57 (1996) Oxford University Press.

Sekiguchi and Shuman, "Proteolytic footprinting of vaccinia topoisomerase bound to DNA," *J. Biol. Chem..* 270(19):11636–45 (1995) The American Society for Biochemistry and Molecular Biology, Inc.

Sekiguchi and Shuman, "Requirements for noncovalent binding of vaccinia topoisomerase I to duplex DNA," *Nucleic Acids Res.* 22(24):5360–5 (1994) Oxford University Press.

Sekiguchi and Shuman, "Stimulation of vaccinia topoisomerase I by nucleoside triphosphates," *J. Biol. Chem.* 269(47):29760–4 (1994) The American Society for Biochemistry and Molecular Biology, Inc.

Sekiguchi and Shuman, "Vaccinia topoisomerase binds circumferentially to DNA," *J. Biol. Chem.* 269(50):31731–4 (1994) The American Society for Biochemistry and Molecular Biology, Inc.

Sekiguchi, et al., "Resolution of a Holliday junction by vaccinia topoisomerase requires a spacer DNA segment 3'of the CCCTT/ cleavage sites," *Nucleic Acids Res.* 28(14):2658–63. (2000) Oxford University Press.

Sekiguchi, et al., "Kinetic analysis of DNA and RNA strand transfer reactions catalyzed by vaccinia topoisomerase," *J. Biol. Chem..* 272(25):15721–8 (1997) The American Society for Biochemistry and Molecular Biology, Inc.

Sekiguchi, et al., "Mechanism of inhibition of vaccinia DNA topoisomerase by novobiocin and coumermycin," *J. Biol. Chem.* 271(4):2313–22 (1996) The American Society for Biochemistry and Molecular Biology, Inc.

Sekiguchi, et al., "Resolution of Holliday junctions by eukaryotic DNA topoisomerase I," *Proc. Natl. Acad. Sci. U S A.* 93(2):785–9. (1996) National Academic of Sciences.

Shuman, "Analysis of topoisomerase–DNA interactions by electrophoretic mobility shift assay," *Methods Mol. Biol.* 95:65–74(2001) Humana Press, Inc.

Shuman, "Polynucleotide ligase activity of eukaryotic topoisomerase I," *Mol. Cell.* 1(5):741–8. (1998) Cell Press.

Shuman, "Vaccinia virus DNA topoisomerase: a model eukaryotic type IB enzyme," *Biochim. Biophys. Acta.* 1400(1–3):321–37. (1998) Elsevier Science.

Shuman, "Vaccinia virus DNA ligase: specificity, fidelity, and inhibition," *Biochemistry* 34:16138–16147 (1995) American Chemical Society.

Shuman, "Novel approach to molecular cloning and polynucleotide synthesis using vaccinia DNA topoisomerase" *J. Biol. Chem..* 269(51):32678–32684 (1994).

Shuman, "DNA Strand Transfer Reactions Catalyzed by Vaccinia Topoisomerase I", *J. Biol. Chem.* 267:8620–8627. (1992) The American Society for Biochemistry and Molecular Biology, Inc.

Shuman, "Two Classes of DNA End–Joining Reactions Catalyzed by Vaccinia Topoisomerase I", *J. Biol. Chem..* 267:16755–16758. (1992) The American Society for Biochemistry and Molecular Biology, Inc.

Shuman, "Recombination mediated by vaccinia virus DNA topoisomerase I in *Escherichia coli* is sequence specific," *Proc. Natl. Acad. Sci. U S A.* 88(22):10104–8 (1991) National Academic of Sciences.

Shuman, "Site–specific DNA cleavage by vaccinia virus DNA topoisomerase I. Role of nucleotide sequence and DNA secondary structure," *J. Biol. Chem.* 266(3):1796–1803 (1991) The American Society for Biochemistry and Molecular Biology, Inc.

Shuman, "Site–specific interaction of vaccinia virus topoisomerase I with duplex DNA. Minimal DNA substrate for strand cleavage in vitro," *J. Biol. Chem.* 266(17):11372–11379 (1991) The American Society for Biochemistry and Molecular Biology, Inc.

Shuman, "Vaccinia DNA topoisomease I promotes illegitimate recombination in *Escherichia coli,*" *Proc. Natl. Acad. Sci. U S A.* 86(10):3489–93 (1989) National Academic of Sciences.

Shuman and Moss, "Identification of a Vaccinia Virus Gene Encoding a Type I DNA Topoisomerase," *Proc. Natl. Acad. Sci., U S A* 84:7478–7482. (1987) National Academic of Sciences.

Shuman and Prescott. "Specific DNA Cleavage and Binding of Vaccinia Virus DNA Topoisomerase I" *J. Biol. Chem.*. 265:17826–17836. (1990) The American Society for Biochemistry and Molecular Biology, Inc.

Shuman and Turner, "Site–specific interaction of vaccinia virus topoisomerase I with base and sugar moieties in duplex DNA," *J. Biol. Chem*. 268(25):18943–50 (1993) The American Society for Biochemistry and Molecular Biology, Inc.

Shuman, et al., "Intramolecular synapsis of duplex DNA by vaccinia topoisomerase," *EMBO J*. 16(21):6584–9 (1997) Oxford University Press.

Shuman, et al., "Insertional mutagenesis of the vaccinia virus gene encoding a type I DNA topoisomerase: evidence that the gene is essential for virus growth," *Virology*. 170(1):302–6 (1989) Academic Press, Inc.

Shuman, et al., "Mapping the active–site tyrosine of vaccinia virus DNA topoisomerase I," *Proc. Natl. Acad. Sci. U S A*. 86(24):9793–7 (1989) National Academic of Sciences.

Shuman, et al., "Characterization of Vaccinia Virus DNA Topoisomerase I Expressed in *Escherichia coli*", *J. Biol. Chem.*. 263:16401–16407. (1988) The American Society for Biochemistry and Molecular Biology, Inc.

Stivers, et al., "Stereochemical outcome and kinetic effects of Rp– and Sp–phosphorothioate substitutions at the cleavage site of vaccinia type I DNA topoisomerase," *Biochemistry* 39(18):5561–72. (2000) American Chemical Society.

Stivers et al., "Vaccinia DNA topoisomerase I: kinetic evidence for general acid–base catalysis and a conformational step," *Biochemistry* 33(51):15449–58 (1994) American Chemical Society.

Stivers, et al., "Vaccinia DNA topoisomerase I: single–turnover and steady–state kinetic analysis of the DNA strand cleavage and ligation reactions," *Biochemistry* 33(1):327–39 (1994) American Chemical Society.

Wang and Shuman, "Deletions at the carboxyl terminus of vaccinia DNA topoisomerase affect DNA binding and enhance distributivity in DNA relaxation," *Biochemistry* 36(13):3909–16 (1997) American Chemical Society.

Wang, et al., "Mutational analysis of 26 residues of vaccinia DNA topoisomerase identifies Ser–204 as important for DNA binding and cleavage," *Biochemistry* 36(26):7944–50 (1997) American Chemical Society.

Wittschieben and Shuman, "Mechanism of DNA transesterification by vaccinia topoisomerase: catalytic contributions of essential residues Arg–130, Gly–132, Tyr–136 and Lys–167," *Nucleic Acids Res*. 25(15):3001–8. (1997) Oxford University Press.

Wittschieben and Shuman, "Mutational analysis of vaccinia DNA topoisomerase defines amino acid residues essential for covalent catalysis," *J. Biol. Chem*. 269(47):29978–83 (1994) The American Society for Biochemistry and Molecular Biology, Inc.

Wittschieben, et al., "Replacement of the active site tyrosine of vaccinia DNA topoisomerase by glutamate, cysteine or histidine converts the enzyme into a site–specific endonuclease," *Nucleic Acids Res*. 26(2):490–6. (1998) Oxford University Press.

Woodfield, et al., "Vaccinia topoisomerase and Cre recombinase catalyze direct ligation of activated DNA substrates containing a 3'–para–nitrophenyl phosphate ester," *Nucleic Acids Res*. 28(17):3323–31 (2000) Oxford University Press.

Yang, et al., "A eukaryotic enzyme that can disjoin dead–end covalent complexes between DNA and type I topoisomerase," *Proc. Natl. Acad. Sci. U S A*. 93(21):11534–9 (1996) National Academic of Sciences.

Liu, et al., "Mapping the 5'and 3'Ends of Tetrahymena thermophila mRNAs Using RNA Ligase Mediated Amplification of cDNA Ends (RLM–RACE)," *Nucleic Acids Research* 21(21): 4954–4960. (1993) The Oxford University Press.

Lockard, et al., "Labeling of Eukaryotic Messenger RNA 5'Terminus with Phosphorus–32: Use of Tobacco Acid Pyrophosphatase for Removal of Cap Structures," *Gene Amplification and Analysis* 2:229–251. (1981) Elsevier Science.

Wexler, et al., "A Procedure to Amplify cDNA from dsRNA Templates Using the Polymerase Chain Reaction," *Methods in Molecular and Cellular Biology* 2:273–279 (1991).

Yarovinsky, Timur O., "Application of DNA Topoisomerase–Activated Adapters to Riboprobe Synthesis," BioTechniques, vol. 28, Jun. 2000, pp. 1160–1165.

Heyman et al., "Genome–Scale Cloning and Expression of Individual Open Reading Frames Using Topoisomerase I–Mediated Ligation," *Genome Research*, pp 383–392 (1999).

Arnott et al., "DNA–RNA Hybrid Secondary Structures," *J. Mol. Biol.*, vol. 188, pp. 631–640 (1986).

Chong et al., "Single–column purification of free recombinant proteins using a self–cleavable affinity tage derived from a protein splicing element", *Gene*, vol. 192, pp. 271–281 (1997).

Matthews et al., "Analytical Strategies for the Use of DNA Probes", *Anal. Biochem.*, vol. 169, pp. 1–25 (1988).

Sambrook et al., *Molecular Cloning–A Laboratory Manual*, 2nd Ed., Cold Springs Harbor Laboratory Press, pp. 2.53–2.54, 16.8–16.9, 16.20 and 16.22 (1989).

Shatkin, "Capping of Eucaryotic mRNAs", *Cell*, vol. 9, pp. 645–653 (1976).

Theus et al., "A Simple Assay for Determining the Capping Efficiencies of RNA Polymerases Used for *In Vitro* Transcription", *Bio Techniques*, vol. 9, pp. 610–615 (1990).

Zechiedrich et al., "Topoisomerase IV, not gyrase, decatenates products of site–specific recombination in *Escherichia coli*", *Genes & Development*, vol. 11, pp. 2580–2592 (1997).

Cormack et al., "Rapid amplification of genomic ends (RAGE) as a simple method to clone flanking genomic DNA", *Gene*, Jul 1997, 194(2):273–6.

Heyman et al., "Genome–scale cloning and expression of individual open reading frames using topoisomerase I–mediated ligation", *Genome Res*, Apr. 1999, 9(4):383–92.

Schaefer, "Revolutions in rapid amplification of cDNA ends: new strategies for polymerase chain reaction cloning of full–length cDNA ends", *Anal Biochem*, May 1995, 227(2):255–73.

\* cited by examiner

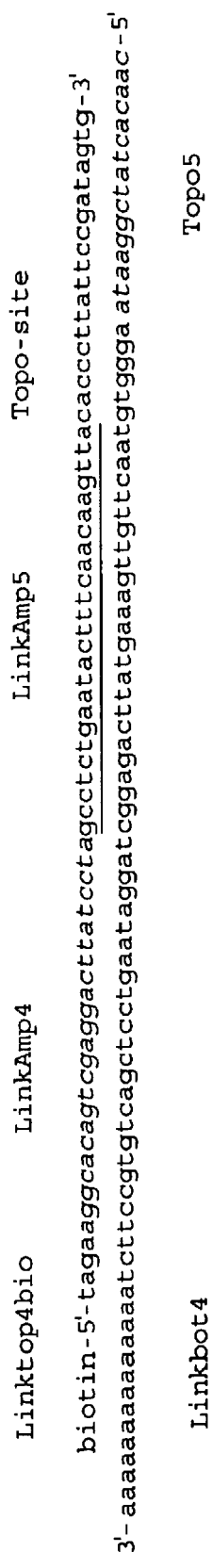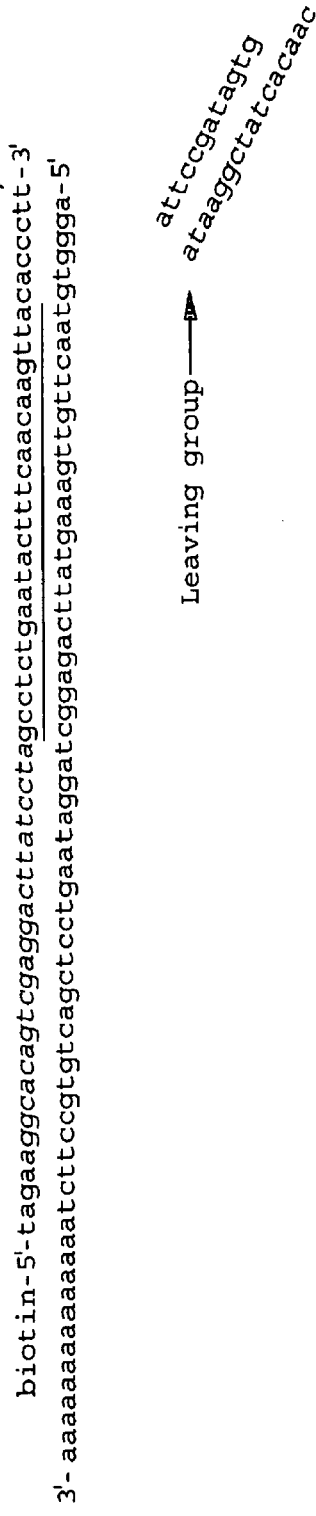

TOPOISOMERASE LINKER-MEDIATED AMPLIFICATION METHODS

This application claims the benefit of priority under 35 U.S.C. §119 of U.S. Ser. No. 60/184,858, filed Feb. 25, 2000, the entire contents of which is incorporated herein by reference.

This invention was made with support under Grant No. 4 R44 CA 80224 from the National Institutes of Health, U.S. Department of Health and Human Services. Accordingly, the United States Government has certain rights in the invention.

FIELD OF THE INVENTION

The present invention generally relates to methods for isolating and sequencing nucleic acid sequences. More particularly, the present invention relates to methods for contiguous sequencing of long DNA containing unknown sequence using a modification of standard PCR techniques.

BACKGROUND OF THE INVENTION

PCR techniques enable the amplification of DNA which lies between two regions of known sequence (K. B. Mullis et al., U.S. Pat. Nos. 4,683,202 and 4,683,195). Oligonucleotides complementary to these known sequences at both ends serve as "primers" in the PCR procedure. Double stranded target DNA is first melted to separate the DNA strands, and then oligonucleotide (oligo) primers complementary to the ends of a target segment whose amplification is desired are annealed to the template DNA. The oligos serve as primers for the synthesis of new complementary DNA strands, using a DNA polymerase enzyme and a process known as primer extension. The orientation of the primers with respect to one another is such that the 5' to 3' extension product from each primer contains, when extended far enough, a segment of sequence that is complementary to the other oligo. Thus, each newly synthesized DNA strand becomes a template for synthesis of another DNA strand beginning with the other oligo as primer. Repeated cycles of melting, annealing of oligo primers, and primer extension lead to a (near) doubling, with each cycle, of DNA strands containing the sequence of the template beginning with the sequence of one oligo and ending with the sequence of the other oligo.

The key requirement for this exponential increase of template DNA is that the two oligo primers are complementary to the ends of the sequence desired to be amplified, and are oriented such that their 3' extension products proceed toward each other. If the sequence at both ends of the segment to be amplified is not known, complementary oligos cannot be made and standard PCR cannot be performed. Thus, this procedure is impractical for contiguously sequencing a long DNA strand, such as a chromosome. Accordingly, an object of the present invention is to overcome the need for sequence information at both ends of the segment to be amplified, i.e. to provide a method that allows PCR to be performed when sequence is known for only a single region, and to provide a method for the contiguous sequencing of a very long DNA without the need for subcloning of the DNA.

DNA sequencing is a technique by which the four DNA nucleotides (characters) in a linear DNA sequence are ordered by chemical and biochemical means. There are two techniques: 1) the chemical method of Maxam and Gilbert (A. M. Maxam, and W. Gilbert, *P.N.A.S. USA*, 74:560–564, 1977), and the enzymatic method of Sanger and colleagues (F. Sanger, S. Nicklen, and A. R. Coulson, 74:5463–5467, 1977). In the chemical method, the DNA strand is isotropically labeled on one end, broken down into smaller fragments at sequence locations ending with a particular nucleotide (A, T, C, or G) by chemical means, and the fragments ordered based on this information. The four nucleotide-specific reaction products are resolved on a polyacrylamide gel, and the autoradiographic image of the gel is examined to infer the DNA sequence.

In the enzymatic method, an oligonucleotide primer is annealed to a suitable single or denatured double stranded DNA template; the primer is extended with DNA polymerase in four separate reactions, each containing one a-labeled dNTP or dideoxynucleoside-5'-triphosphate (ddNTP) (alternatively a labeled primer can be used), a mixture of unlabeled dNTPs, and one chain-terminating ddNTP; resolving the four sets of reaction products on a high resolution polyacrylamide-urea gel; and producing an autoradiographic image of the gel that can be examined to infer the DNA sequence. Alternatively, fluorescently labeled primers or nucleotides can be used to identify the reaction products. Known dideoxy sequencing methods utilize a DNA polymerase such as the Klenow fragment of *E. coli* DNA polymerase, reverse transcriptase, a modified T7 DNA polymerase, or the Taq polymerase.

The PCR amplification procedure has been used to sequence DNA being amplified (e.g. using AmpliTaq ™DNA polymerase Cycle Sequencing (Perkin Elmer Cetus Corporation)). By this procedure, DNA can be first amplified and then sequenced using the two conventional DNA sequencing techniques. A modification of this procedure is disclosed by Bevan et al., *PCR Meth. App.* 4:222 (1992)). The PCR method also enables the reduction of non- specific binding of the printers to the template DNA because the enzymes used in these protocols function at high-temperatures, and thus allow "stringent" reaction conditions to be used to improve sequencing. By this procedure, DNA can be first amplified and then sequenced using the two conventional DNA sequencing techniques. A modification of this procedure is disclosed by Bevan et al., *PCR Meth. App.* 4:222 (1992)). The PCR method also enables the reduction of non-specific binding of the primers to the template DNA because the enzymes used in these protocols function at high-temperatures, and thus allow "stringent" reaction conditions to be used to improve sequencing.

In the currently existing methods for sequencing DNA of millions of nucleotides, the DNA is fragmented into smaller, overlapping fragments, and sub-cloned to produce numerous clones containing overlapping DNA sequences. These clones are sequenced randomly (sometimes known as the "shot-gun sequencing method") and the sequences are assembled by "overlap sequence-matching" to produce the contiguous sequence. In this shot-gun sequencing method, approximately ten times more sequencing than the length of the DNA being sequenced is required to assemble the contiguous sequence. In these sequencing methods, the linear order of the DNA clones has to be first determined by "physical mapping" of the clones.

Among the currently known contiguous DNA sequencing methods is a procedure called the "primer-walking" or "chromosome walking" method, which uses Sanger's DNA polymerase enzymatic sequencing procedure. In this method, however, the DNA copying always has to occur from the template DNA during DNA sequencing (rather than from the target DNA amplified in the first rounds from the original input template DNA functioning as the template DNA for subsequent cycles of amplification, as in PCR sequencing). Thus, in the "primer-walking" or "chromosome walking" method, after a certain number of cycles of amplification, the DNA sequencing reaction is initiated by adding a sequencing "cocktail". As a result, the "primer-walking" or "chromosome walking" method requires a larger amount of template DNA than does the PCR sequencing method. Also, when a very long DNA is being sequenced, the DNA has a tendency to re-anneal back to duplex DNA, so that the sequencing gel pattern obtained by the "primer-walking" method may not be as clean as in a PCR procedure. This disadvantage may limit the length of the DNA that can be contiguously sequenced by this method without breaking the DNA.

U.S. Pat. No. 5,994,058 discloses a method for sequencing long nucleotide molecules using the PCR procedure wherein the sequence of only one primer needs to be known. In this method a first primer is used that is fully complementary to a primer binding site on the target nucleic acid sequence and the second primer consists of 12–16 nucleotides of which 1–10 of the nucleotides anywhere within the primer are of fixed sequence while the remaining nucleotides of the second primer are of random sequence. By generating a large enough number of such second primers of various sequence, one will have a nucleotide sequence fully complementary to a second primer binding site. Using this technique, a long genomic DNA, such as a chromosome, can be contiguously sequenced without the need for subcloning it into smaller fragments. However, in this method, a very large number of second primers must be generated, only a few of which will prove useful.

A combination of "shotgun sequencing" and "chromosome walking" is also currently used to enable the isolation of unknown DNA through use of the adjacent DNA's known sequence. These techniques are routinely applied during analysis of genomic DNA. For example, high-throughput "shotgun sequencing" invariably reaches a stage at which continued sequencing of random clones becomes an inefficient method to close gaps in assembled sequence. When these gaps are too large for standard PCR amplification, "chromosome walking" may be used to systematically obtain and sequence DNA spanning the gaps.

Vaccinia DNA topoisomerase has been used in procedures involving the joining of DNA fragments. Vaccinia DNA topoisomerase, a 314 aa virus-encoded eukaryotic type I topoisomerase (I), binds to duplex DNA and cleaves the phosphodiester backbone of one strand (Shuman, S., and Moss, B. (1987) Proc. Natl. Acad. Sci. USA 84: 7478–7482). The enzyme exhibits a high level of sequence specificity, akin to that of a restriction endonuclease. Cleavage occurs at a consensus pentapyrimidine element 5'-(C/T)CCTT-3' in the scissile strand (Cheng, S., et al. (1994) Proc. Natl. Acad. Sci. USA 91: 5695–5699; Clark, J. M. (1988) Nucleic Acids Res. 16: 9677–9686; and Morham, S. G., and Shuman, S. (1992) J. Biol. Chem. 267: 15984–15992). In the cleavage reaction, bond energy is conserved via the formation of a covalent adduct between the 3' phosphate of the incised strand and a tyrosyl residue (Tyr-274) of the protein. Vaccinia topoisomerase can religate the covalently held strand across the same bond originally cleaved (as occurs during DNA relaxation) or it can religate to a heterologous acceptor DNA and thereby create a recombinant molecule.

The repertoire of DNA joining reactions catalyzed by Vaccinia topoisomerase has been studied in detail by Dr. Stewart Shuman using synthetic duplex DNA substrates containing a single CCCTT cleavage site. When the substrate is configured such that the scissile bond is situated near (e.g., within 10 bp of) the 3' end of a DNA duplex, cleavage is accompanied by spontaneous dissociation of the downstream portion of the cleaved strand (Shuman, S., J. Biol. Chem. 267:8620–8627, 1992a; Shuman, S., J. Biol. Chem. 267:16755–16758, 1992b). The resulting topoisomerase-DNA complex, containing a 5' single-stranded tail, can religate to an acceptor DNA if the acceptor molecule has a 5' hydroxyl tail complementary to that of the activated donor complex. Sticky end-ligation by Vaccinia topoisomerase has also been demonstrated by Shuman, using plasmid DNA acceptors with four base overhangs created by restriction endonuclease digestion.

PCR fragments are naturally good surrogate substrates for the topoisomerase I religation step because they generally have 5' hydroxyl residues from the primers used for the amplification reaction. The 5' hydroxyl is the substrate for the religation reaction. U.S. Pat. No. 5,766,891 discloses a method utilizing this feature of topoisomerase religation to ligate duplex DNAs employing the modified tagged Vaccinia topoisomerase. In this method of ligation the donor duplex DNA substrate is a bivalent donor duplex DNA substrate, that is, it contains two topoisomerase cleavage sites. One embodiment comprises cleaving a donor duplex DNA substrate containing sequence-specific topoisomerase cleavage sites by incubating the donor duplex DNA substrate with a sequence-specific topoisomerase to form a topoisomerase-bound donor duplex DNA strand and incubating the topoisomerase-bound donor duplex DNA strand with a 5' hydroxyl-terminated compatible acceptor DNA, resulting in the ligation of the topoisomerase-bound donor duplex DNA strand to the DNA acceptor strand.

Despite these advancements in the art, there is a need for new and better methods for isolating and sequencing long stretches of nucleic acid containing segments of unknown sequence. In particular, there is a need in the art for an efficient method for systematically obtaining and sequencing DNA spanning the gaps in a sequence assembled by high-throughput "shotgun sequencing."

SUMMARY OF THE INVENTION

The present invention overcomes many of the problems in the art by providing an efficient linker-assisted amplification method for isolating and, optionally, contiguous sequencing of an oligonucleotide using basic PCR techniques. The invention is based upon the discovery that Vaccinia Topoisomerase I can be used to specifically join a duplex linker containing an oligonucleotide primer binding site to the end of a desired DNA fragment having unknown sequence, allowing subsequent PCR amplification. Invention constructs and methods are particularly useful when the sequence of one primer to be used in the PCR amplification is known and nothing is known about the sequence needed for the other primer. Thus, the invention provides methods and constructs useful for systematically obtaining and sequencing DNA, such as that spanning the gaps in a sequence assembled by high-throughput "shotgun sequencing."

In one embodiment according to the present invention, there are provided double stranded topoisomerase-adapted linkers for use in linker-mediated PCR amplification methods. The invention topoisomerase-adapted linkers comprise a duplex oligonucleotide linker wherein a first oligonucleotide is annealed to a second oligonucleotide that is phosphorylated at the 5' end thereof and wherein the linker further comprises a compatible site-specific topoisomerase enzyme covalently attached to the first oligonucleotide at a single base 3' T overhang.

In another embodiment according to the present invention, there are provided methods for isolating a target polynucleotide having a segment of unknown sequence when sequence of adjacent nucleic acids is known. The invention method comprises cutting the target polynucleotide with a restriction endonuclease that leaves a 3' overhang of at least 2 bases to obtain an overhang-digested polynucleotide segment, dephosphorylating the 5' ends of the overhang-digested polynucleotide segment, performing a Taq polymerase mediated primer extension of the 5' dephosphorylated overhang-digested polynucleotide segment using a sequence-specific primer to create a duplex extension product having at the 3' ends a single A base overhang, incubating the duplex extension product with an invention topoisomerase-adapted linker so as to selectively attach the duplex DNA of the linker to the extension product to form a linked extension product, and isolating a second extension product produced by amplifying the linked extension product using the sequence-specific primer and a topoisomerase linker-specific primer. Since a sequence-specific primer is used in PCR amplification of the overhang-digested polynucleotide segment, it is generally preferred to cut the target polynucleotide in an segment of the oligonucleotide of known sequence.

The sequence-specific primers used in the invention methods should be oligonucleotides designed to anneal to the target polynucleotide as close to the unknown sequence as possible, they should not overlap, and should have a melting temperature of at least 56° C. so that stringent hybridization conditions can be used during PCR reactions.

In another embodiment according to the present invention, there are provided methods for contiguous sequencing of genomic DNA having a segment of unknown sequence in a vector. In this embodiment, the invention method comprises cutting the nucleotide sequence of the vector with a restriction endonuclease that leaves a 3' overhang of at least 2 bases to obtain an overhang-digested polynucleotide segment that contains an oligonucleotide of unknown sequence, dephosphorylating the 5' ends of the overhang-digested polynucleotide segment, performing a Taq polymerase mediated primer extension of the 5'-dephosphorylated overhang-digested polynucleotide segment using a vector sequence-specific primer to create a duplex extension product having at the 3' ends a single A base overhang, incubating the duplex extension product with an invention topoisomerase-adapted linker so as to selectively join the duplex DNA contained in the linker to the extension product to form a linked extension product, and isolating a second extension product produced by amplifying the linked extension product using the vector sequence-specific primer and a topoisomerase linker-specific primer.

In another embodiment according to the present invention, there are provided kits for contiguous sequencing of genomic DNA that is cloned in a vector. The invention kit comprises an invention topoisomerase-adapted linker and a topoisomerase linker-specific oligonucleotide, wherein the linker-specific oligonucleotide hybridizes with the duplex DNA of the linker under stringent conditions.

In another embodiment according to the present invention, there are provided methods for amplifying by the polymerase chain reaction (PCR) a portion of a target polynucleotide, said method comprising cutting the target polynucleotide with a restriction endonuclease that leaves a 3' overhang of at least 2 bases to obtain an overhang-digested polynucleotide segment, removing the 5' phosphate groups from the overhang-digested polynucleotide segment, performing a Taq polymerase-mediated primer extension of the overhang-digested polynucleotide segment using a sequence-specific primer to create a duplex extension product having at the 3' ends a single A base overhang, incubating the duplex extension product with a topoisomerase-adapted linker as described herein so as to covalently attach the duplex DNA of the linker to the extension product to form a linked extension product, and performing PCR amplification of the linked extension product using the sequence-specific primer and a topoisomerase linker-specific primer.

BRIEF DESCRIPTION OF THE FIGURE

FIGS. 1A and 1B are schematic illustrations of invention linker duplex oligonucleotides before (FIG. 1A) and after (FIG. 1B) covalent attachment of Vaccinia Topoisomerase I. Names of oligos used to create the pro-linker are in bold. Topo5 (sequence in bold italics) (SEQ ID NO: 1) anneals to Linktop4bio (SEQ ID NO: 2) as shown. The arrow in FIG. 1A indicates the break point in the pro-linker at which there is no bond between Topo5 and Linkbot4 (SEQ ID NO: 3). After topoisomerase I makes its covalent attachment to the 3'T residue in the topoisomerase cleavage site (in bold), the double-stranded DNA 3' of this site is the leaving group. LinkAmp4 (sequence shown in italics) and Link Amp5 (underlined) anneal to Linkbot4 as shown. Topoisomerase I covalently attaches to a single base 3' overhang at one end of the cleavage site to create the invention linker topoisomerase-adapted linker as shown in FIG. 1B.

DETAILED DESCRIPTION OF THE INVENTION

In accordance with the present invention, there are provided double stranded topoisomerase-adapted linkers for use in linker-mediated PCR amplification methods. The invention topoisomerase-adapted linkers comprise a duplex oligonucleotide linker wherein a first oligonucleotide is annealed to a second oligonucleotide that is phosphorylated at the 5' end thereof and wherein the linker further comprises a compatible site-specific topoisomerase enzyme covalently attached to the first oligonucleotide at a single base 3' T overhang.

The site-specific topoisomerase enzyme contained within the invention linkers can be any site-specific type I topoisomerase. Topoisomerases are a class of enzymes that modify the topological state of DNA via the breakage and rejoining of DNA strands. For example, Vaccinia topoisomerase enzyme is a 314 aa type I topoisomerase encoded by a Vaccinia virus. Site-specific type I topoisomerases include, but are not limited to, viral topoisomerases such as pox virus topoisomerases. Examples of pox virus topoisomerases include shope fibroma virus and ORF virus. Other site specific topoisomerases and the cleavage sites to which they bind are known to those skilled in the art.

A "compatible site-specific topoisomerase enzyme," as the term is used herein with reference to the invention linker, means a topoisomerase enzyme that recognizes the cleavage site in the invention linker. Preferably, the invention linker comprises the cleavage site for Vaccinia topoisomerase and the site-specific topoisomerase enzyme is Vaccinia topoisomerase.

Vaccinia topoisomerase binds to duplex DNA and cleaves the phosphodiester backbone of one strand while exhibiting a high level of sequence specificity, cleaving at a consensus pentapyrimidine element 5'-(C/T)CCTT (SEQ ID NO: 4), or related sequences, in the scissile strand. Examples of alternative Vaccinia topoisomerase cleavable sequences are disclosed in U.S. Pat. No. 5,766,891, which is incorporated herein by reference in its entirety, and include duplex 5'-GCCCTTATTCCC (SEQ ID NO: 5), duplex 5'-TCGCCCTTATTC (SEQ ID NO: 6), duplex TGTCGC-CCTTAT (SEQ ID NO: 7), and duplex GTGTCGC-CCTTA (SEQ ID NO: 8).

The phospho-tyrosyl bond between the DNA and enzyme can subsequently be attacked by the 5' hydroxyl of the original cleaved strand, thus reversing the reaction and releasing the topoisomerase. Because topoisomerase catalyzes both cleavage and religation, the structures in FIGS. 1A and 1B will reach an equilibrium. To assure covalent attachment of the Vaccinia topoisomerase to the duplex DNA during formation of the linker (and prevent religation of the cleaved strand), the 5' end of the second nucleotide in the duplex strand of the pro-linker (shown in FIG. 1A) is phosphorylated at the 5' end thereof, driving the reaction towards the cleaved product. Once the Vaccinia topoisomerase enzyme is covalently attached to the linker and the leaving group is separated from the pro-linker, the reaction is virtually quantitative and irreversible until an acceptor DNA is provided (i.e., a duplex DNA having a single 3'A base overhang).

A "pro-linker" as the term is used herein, refers to an annealed duplex oligonucleotide (e.g., DNA) substrate that a compatible site-specific Topoisomerase I can cleave and to which the Topoisomerase I will covalently attach at the point of cleavage to yield the invention topoisomerase-adapted linker. Therefore, the pro-linker is a duplex oligonucleotide wherein the first oligonucleotide contains the topoisomerase cleavage site at or near the '3 end thereof, depending upon the preference of the particular topoisomerase used, and the second oligonucleotide is adapted to force the reversible reaction of the topoisomerase with the pro-linker so as to yield the topoisomerase-adapted linker. For example, if the topoisomerase to be used in fabrication of the invention topoisomerase-adapted linker is Vaccinia topoisomerase, the cleavage site (SEQ ID NO: 4) is located within about 2 to about 12 bp from the 3' end of the first oligonucleotide in the pro-linker and the second oligonucleotide in the pro-linker is phosphorylated at the 5' end thereof to prevent religation of the leaving group to reform the pro-linker duplex DNA. The method of making the invention topoisomerase-adapted linker is fully illustrated in Example 1 herein. Preferably, the first oligonucleotide in the invention pro-linker will contain a sequence comprising the cleavage site for a Topoisomerase I within about 2 to 12 bases of the 3' end.

Incubation of the pro-linker with the compatible site-specific topoisomerase under suitable conditions, as known in the art, will cause the enzyme to cleave the duplex DNA of the pro-linker at the cleavage site, and covalently attach to the 3' end of the cleavage site therein, forming the invention topoisomerase-adapted linker. Other than these requirements, there is no restriction placed on the number or composition (i.e. nucleotide sequence) of the two oligonucleotides in the linker, except that they must be selected so that the two oligonucleotides will anneal and remain annealed during attachment of the topoisomerase to the pro-linker. Preferably the two oligonucleotides in the duplex linker are fully complementary and the melting temperature of the linker is at least about 56° C.

Thus, the length and nucleotide composition of the two oligonucleotides in the invention linker can be selected for convenience in avoiding unwanted effects that might result from incorporating into the linker an undesirable endonuclease site. However, it should also be kept in mind, that, when transferred to the acceptor end of DNA by action of the enzyme, the linker provides a target annealing site for the "second primer" (i.e., the linker-specific primer) for purposes of performing PCR amplification of a the linked segment of DNA. Consequently, all or any part of the oligonucleotides in the invention linker can serve as an annealing site for one or more linker-specific primers used in the invention methods as described herein.

For example, in a preferred embodiment according to the invention, the first oligonucleotide in the invention topoisomerase-adapted linker comprises a first oligonucleotide sequence
5'-TAGAAGGCACAGTCGAGGACTTATCCTAGCCT-CTGAATACTTTC AACAAGTTA-3'(SEQ ID NO: 9) and is adapted at the 5' end with an affinity tag, such as biotin, or a detectable molecule, such as a fluorescent molecule, to aid in selection of a polynucleotide to which the topoisomerase has transferred the invention linker from a heterogeneous mixture of polynucleotides. The biotin affinity tag also prevents the 5' end of the oligo from being a substrate for topoisomerase-mediated end-joining. In addition, the biotin modification facilitates reverse-phase chromatography oligo purification, eliminating the need for more costly gel-purification. The biotin group may also be useful in purifying the linked product before PCR by binding the biotin-ligated product to streptavidin. Other purification methods are known to those skilled in the art.

The second oligonucleotide is preferably fully complementary to the first nucleotide in the linker duplex and is phosphorylated at the 5' end thereof to ensure that it will not be a substrate for Topo-mediated DNA end-joining. For use with the first oligonucleotide having a sequence according to SEQ ID NO: 9, the second oligonucleotide in the linker can have the sequence:
5'-AGGGTGTAACTTGTTGAAAGTATTCAGAGGCT-AGGATAAGTCCT CGACTGTGCCTTCT-3'(SEQ ID NO: 10)

Optionally the second oligonucleotide further comprises a 3' polyadenylation tail to aid in removal of the second oligonucleotide from a heterogeneous mixture of polynucleotides, as in the oligonucleotide:
5'-AGGGTGTAACTTGTTGAAAGTATTCAGAGGCT-AGGATAAGTCCT CGACTGTGCCTTCTAAAAAAAAAAAAAAA-3' (SEQ ID NO: 3). The polyA stretch has been shown to bind oligodT cellulose to aid in preparation of the linker.

For use with a linker containing the above described first and second oligonucleotides, in the invention methods, linker-specific primers having the sequence:
5'-TAGAAGGCACAGTCGAGGACTTATCCTA-3' (SEQ ID NO: 11), which anneals to the 5' end of the second oligonucleotide in the linker, or 5'-GCCTCTGAATACTTTCAACAAGTTA-3' (SEQ ID NO: 12), which anneals to the area 3' of the target site of SEQ ID NO:3 can be used. The latter of the two linker-specific primers is particularly designed for use with the above described linker in nested PCR as the internal linker-specific primer.

Those of skill in the art will appreciate that, in general, the oligonucleotide sequence of linker-specific primers used for linker-mediated PCR amplification according to the invention methods will be designed to hybridize to whatever particular second oligonucleotide is used in the duplex linker under the conditions used for conducting the linker-mediated PCR amplification. For example, stringent conditions can be used, such as are commonly used for Taq polymerase mediated primer extension, as is known in the art and as further illustrated in the Examples herein.

In another embodiment according to the present invention, there are provided methods for isolating a target polynucleotide having a segment of unknown sequence when sequence of some portion of the target polynucleotide is known, e.g., an adjacent segment of the target polynucleotide. The invention linker-assisted isolation method comprises:

(a) cutting the target polynucleotide with a restriction endonuclease that leaves a 3' overhang of at least 2 bases to obtain an overhang-digested polynucleotide segment, (b) dephosphorylating the 5' ends of the overhang-digested polynucleotide segment, (c) performing a Taq polymerase mediated primer extension of the 5'-dephosphorylated overhang-digested polynucleotide segment using a sequence-specific primer to create a duplex extension product having at the 3' ends a single A base overhang, (d) incubating the duplex extension product with an invention topoisomerase-adapted linker so as to selectively attach the duplex DNA of the linker to the extension product to form a linked extension product, and (e) isolating a second extension product produced by amplifying the linked extension product using the sequence-specific primer and a topoisomerase linker-specific primer.

The dephosphorylated, A-tailed polynucleotide segments produced in step (d) of the invention method are the only acceptor sites for ligation of the invention Topoisomerase I adapted linker, allowing for specific ligation of the linker to the 3' ends of the polynucleotide segments prior to linker-mediated PCR amplification thereof. Therefore, in the use of invention methods to determine the sequence of an unknown segment of a target oligonucleotide, it is important to use a restriction endonuclease in step (a) of the invention method that cuts the target polynucleotide in the segment of unknown sequence. The preferred phosphatase for dephosphorylating the 5' ends of the cut DNA is calf intestinal phosphatase.

Optionally, the invention method may further comprise the step of obtaining the sequence of the isolated second extension product. It is presently preferred that the second extension product be gel-purified using fast performance liquid chromatography (FPLC) prior to sequencing. Thus, the invention methods of linker-mediated isolation and sequencing can be used to sequence a nucleic acid having a large segment of unknown sequence without cloning of the second extension product into a vector. Alternatively, the PCR products obtained by the invention methods can be readily cloned into a T/A® cloning vector or TOPO-T/A® cloning vector (Invitrogen, San Diego, Calif.) for subsequent sequencing.

Preferably the nucleic acid sequence is cut to completion with the restriction endonuclease, and the Taq polymerase used in the Taq polymerase mediated primer extension of the overhang-digested nucleic acid sequence is a Taq I polymerase that leaves the 3' ends of the extension products with a single A base overhang at the 3' ends. After dephosphorylation of the 5' ends of the extension product, a duplex extension product with 3' A base overhangs is incubated with the invention topoisomerase-adapted linker so that the enzyme transfers the linker (i.e. in a topoisomerase "religation reaction") to the duplex extension product at the 3' A base overhang ends thereof. Thus, a linked extension product having at the 3' ends thereof a segment of nucleic acid of known sequence (i.e. the invention linker) is provided. In the subsequent round of linker-mediated PCR amplification, a linker-specific oligonucleotide primer is annealed to the linker segment of the linked extension product. A second round of PCR extension, preferably under stringent conditions to assure sequence fidelity in the extension product, provides multiple copies of an isolated oligonucleotide that contains the linker-specific primer at the 3' end thereof.

As those of skill in the art will understand from the above description of the preferred embodiment, if a different sequence-specific topoisomerase is employed that ligates to DNA having a different overhang or other target characteristic, then the polymerase used to prepare the segment of DNA to be amplified is selected to match the requirements of the topoisomerase, thereby causing ligation of the invention linker only to the 3' end of the segment of DNA (i.e., the end of unknown sequence) to be amplified.

In the preferred embodiment of the invention linker-mediated amplification methods, the preferred topoisomerase-adapted linker is adapted by covalent attachment of Vaccinia topoisomerase and the duplex DNA comprises the nucleic acid sequences of SEQ ID NO: 9 and SEQ ID NO: 10 as described in detail above. For invention methods employing this linker, the preferred linker-specific primers are those having the nucleic acid sequence of SEQ ID NO: 11 or SEQ ID NO: 12, or a combination thereof. The linker-specific primer of SEQ ID NO: 11 is preferred for use in nested PCR amplification, since this primer is designed to anneal during PCR to a segment of the linker 3' of the segment to which the linker-specific primer of SEQ ID NO: 12 anneals. Hence it is referred to herein as the "internal linker-specific primer." This linker preferred for use in the practice of the present invention has a length of 58 bp to provide sufficient known sequence for two mutually exclusive target primer annealing sites, but the linker used in accordance with the invention can be of any convenient length so long as it is at least about 15 bp in length (the minimum length of a primer used in PCR amplification being generally about 15 nucleotides). Those of skill in the art will appreciate that in other embodiments of the invention, wherein the oligonucleotides in the duplex linker have a different sequence than in the exemplary preferred embodiment, a similar strategy will be employed wherein the oligonucleotides that make up the duplex linker are designed to provide a known segment of nucleic acid sequence that serves as one or more, preferably mutually exclusive, target sites for annealing of sequence-specific primers during linker-mediated PCR amplification procedures.

If there is one strong PCR product detected by electrophoresis on agarose gel, the product can be gel-purified, preferably using SNAP columns as is known in the art and described in the Examples herein. For sequencing, one of the internal sequence-specific primers or internal linker-specific primers can be used, if desired. If the PCR amplification produces multiple bands on the purification gel, or to confirm the identity of the PCR product before sequencing, the initial amplification product can be diluted, for example in a 1/1000 dilution, and used as template in a nested PCR as described herein using sequence-specific and linker-specific primers that are internal to those used in the initial PCR amplification. This nested PCR amplification preferably will produce a single PCR product that can be purified and sequenced.

The above described linker-mediated amplification methods are specifically designed for contiguous sequencing of genomic DNA of unknown sequence cloned in a vector, such as an artificial chromosome vector, wherein at least some sequence of the vector is known 5' to the clone contained in the vector, e.g., 5' to a cloning site therein. If a vector is used wherein the sequence of the vector is known in the area 5' to a cloning site, it is not necessary to know the sequence of any part of the cloned DNA or RNA nucleotide in order to obtain the sequence thereof. The invention method for linker-mediated amplification and sequencing of genomic DNA of unknown sequence contained in such a vector comprises:

(a) cutting the nucleotide sequence of the vector with a restriction endonuclease that leaves a 3' overhang of at least 2 bases to obtain an overhang-digested polynucleotide segment that contains an oligonucleotide of unknown sequence, (b) dephosphorylating the 5' ends of the overhang-digested polynucleotide segment, (c) performing a Taq polymerase mediated primer extension of the 5'-dephosphorylated overhang-digested polynucleotide segment using a vector sequence-specific primer to create a duplex extension product having at the 3' ends a single A base overhang, (d) incubating the duplex extension product with an invention topoisomerase-adapted linker so as to selectively join the duplex DNA contained in the linker to the extension product to form a linked extension product, and (e) isolating a second extension product produced by amplifying the linked extension product using the vector sequence-specific primer and a topoisomerase linker-specific primer.

The isolated second extension product can be directly sequenced to obtain the complete sequence thereof, preferably after FPLC gel purification, without first cloning the second extension product into a sequencing vector. Thus, in the case where the segment of genomic DNA of unknown sequence is contained within a vector, such as an artificial chromosome vector, the procedure used is similar to that described above wherein the sequence of a portion of a target polynucleotide is known, except that in the present embodiment the portion of target polynucleotide for which sequence is known is contained within the vector and the sequence-specific primer used (i.e., the 5' primer of the extension product) is designed to anneal to a segment of the vector of known sequence (and is therefore referred to herein as a "vector sequence-specific primer") rather than to a segment of the clone. Thus, in this embodiment of the invention, it is possible to isolate and sequence a target polynucleotide for which no sequence information is known.

For nested PCR in such a vector of known sequence, two or more such vector sequence-specific primers that anneal to "nested" segments of vector nucleic acid sequence are designed so that the vector specific primer and linker-specific primer used in the nested PCR amplification are both internal to that used in the primary round of linker-mediated PCR amplification.

The vector is generally an artificial chromosome vector and can be either a bacterial artificial chromosome vector (BAC) or a yeast artificial chromosome vector (YAC), such as a Lambda vector, as illustrated herein in Example 2 below. For example, a unique segment of about 1 kb from a BAC clone that contains a 170 kb human DNA insert has been successfully sequenced using the invention method.

In another embodiment according to the present invention, there are provided kits useful for performing the invention linker-mediated amplification methods. The invention kits comprise an invention topoisomerase-adapted linker and one or more linker-specific primers that will anneal to the vector during PCR amplification. For example, the linker-specific primers can be fully complementary to a sequence of at least 15 contiguous nucleotides contained in the second oligonucleotide in the duplex linker. Preferably, the topoisomerase-adapted linker contained in the invention kit is the 58 bp duplex linker that comprises two oligonucleotide having the sequences of SEQ ID NO: 9 and SEQ ID NO: 10 and is adapted by covalent attachment of Vaccinia topoisomerase as described in detail above and the linker-specific primers contained in the kit are one or both of the oligonucleotides described herein as containing SEQ ID NO: 11 and/or SEQ ID NO: 12.

Optionally, the invention kit may further contain reagents useful for purification and direct sequencing of PCR products as described in the Examples herein. For example, reagents useful for performing NA-Iodide SNAP™gel purification of polynucleotides may optionally be contained in the invention kits and/or reagents useful for performing Taq mediated PCR.

The invention kit is the first to use Topoisomerase I to attach a desired DNA to non-vector DNA, and it is the first to use a tagged Topoisomerase I to select a specific polynucleotide from a heterogeneous mixture of polynucleotides. The kit features a double-stranded DNA oligo that is covalently charged with Vaccinia Topoisomerase I (the topoisomerase-adapted linker) and include reagents for purification and direct sequencing of PCR products. The kit will likely be used for the analysis of genomic DNA elements such as exon-intron junctions and promoter regions. In addition, the kit should provide a rapid method to close gaps in sequence generated through shotgun sequencing.

The present invention methods are not limited to only unknown genomic DNA, and can be used to sequence any DNA or RNA under any situation. DNAs or RNAs of many different origins (e.g. viral, cDNA, mRNA) can be sequenced, not only for research or information gathering purposes, but also for other purposes, such as disease diagnosis and treatment, DNA testing, and forensic applications.

The invention will now be described in greater detail by reference to the following non-limiting examples.

The Examples herein describe a preferred method for manufacture of the invention pro- linker and topoisomerase-adapted linker. This method includes use of polynucleotide kinase (PNK) during the adaptation reaction to improve the efficiency of covalent attachment of Topoisomerase I to a desired DNA. Separation of Topoisomerase I/DNA complexes away from ATP, kinase, and free topoisomerase can then be accomplished using FPLC over a SEPHACRYL S-200 gel column, which is also known to be an effective method to separate Topoisomerase I/DNA complexes away from ATP, kinase, and free topoisomerase.

EXAMPLE 1

Preparation Of A Double-Stranded Topoisomerase I Adapted Linker

A. Oligos Used to Prepare Pro-linker:

Linktop4bio

5'-TAGAAGGCACAGTCGAGGACTTATCCTAGCCT-CTGAATACTTTC AACAAGTTACACCCTTATTCCGAT-AGTG (SEQ ID NO: 2). This oligo contains the Vaccinia Topoisomerase I cleavage site (in bold) and is biotinylated at the 5' end. The biotin prevents the 5' end of the oligo from being a substrate for Topo-mediated end-joining. In addition, the biotin modification facilitates reverse-phase chromatography oligo purification, eliminating the need for more costly gel purification. The biotin group may also be useful in purifying the linked product before PCR.

Linkbot4
5'-p-AGGGTGTAACTTGTTGAAAGTATTCA-GAGGCTAGGATAAGTCC TCGACTGTGCCT-TCTAAAAAAAAAAAAAAA (SEQ ID NO: 3). This oligo is phosphorylated at the 5' end to ensure that it will not be a substrate for topoisomerase-mediated DNA end-joining. The polyA stretch has been shown to bind oligodT cellulose which may provide additional uses in separation of the linker.

Topo5
5'-CAACACTATCGGAATA (SEQ ID NO: 1). This oligo is modified by phosphorylation at the 5' end and anneals to Linktop4bio 3' of the phosphodiester bond cleaved by topoisomerase, to form the "leaving group". The oligos anneal as shown in FIG. 1A to create the pro-linker; the structure of the invention linker after Topoisomerase I adaptation is shown in FIG. 1B.

B. Annealing Reaction:
1. In separate tubes, DNA oligos: biotinylated Linktop4bio, phosphorylated Linkbot4 and Topo5 (described in Section A above) were diluted to concentration $1 \times 10^{-4}$ M in $dH_2O$.
2. The annealing reaction was set up as follows (final concentrations in brackets): 22.2 μg Linktop4bio ($1 \times 10^{-5}$ M), 22.6 μg Linkbot4 ($1 \times 10^{-5}$ M), 5 μg Topo5 ($2 \times 10^{-5}$ M), 3.2 μl 5 M NaCl (160 mM), 1 μl 1 M Tris-Cl, pH 8.0 (10 mM), and $dH_2O$ to 100 μl total volume (total DNA concentration was 534 ng/μl). The mixture was heated to 94° C. and slowly cooled to room temperature, then placed on ice.
3. A diluted stock mixture (5 ng/1) of the annealed oligos to be used as a standard in the QC protocol below was prepared by combining 5 μl of the 534 ng/l mixture with 529 μl tris-EDTA. Subsequently, the annealed oligos, which comprise the invention pro-linker were stored at minus 20° C.

C. Topoisomerase I Adaptation of the Pro-linker:
Topoisomerase I was adapted by mixing 35 μl of the annealed oligos, 87 μg Vaccinia Topoisomerase I, 40 units T4 polynucleotide kinase (NEB), 17.5 μl 10×polynucleotide kinase buffer (10×concentration=700 mM Tris-HCl, pH 7.6; 100 mM $MgCl_2$; 50 mM dithio threitol, 4 μl 100 mM ATP, and $dH_2O$ to a final volume of 175 μl. The mixture was incubated for 2 hours at 37° C. followed by the addition of 3.5 μl 0.5 M ethylenediamine tetraacetic acid EDTA to chelate the magnesium and inhibit possible nuclease activity during subsequent manipulations. In this reaction, the ratio of topoisomerase to topoisomerase cleavage sites in the DNA was approximately 5:1. 20 μl of reaction mixture was saved out for subsequent analysis.

D. Purification of Topoisomerase I Adapted Double-stranded Oligonucleotides ("Topoisomerase-linker")
FPLC gel-filtration purification was performed to separate the covalent Topoisomerase I/DNA complex from the other components of the Topo-adaptation mixture (PNK, ATP, ADP, free topoisomerase I, and free oligonucleotides). Sephacryl S-200, which has a fractionation range for globular proteins of $5 \times 10^3$ to $2.5 \times 10^5$ Daltons and should exclude DNA >30 base pairs, was used as the column matrix. It was thought that this matrix would allow topoisomerase/DNA complexes to elute in or near the void volume, followed by free DNA, free protein, and then ATP. The column volume was ~24 mls and the column buffer was 200 mM NaCl, 1 mM EDTA, 10 mM Tris-Cl pH 8.0. The gel filtration column was run at 0.3 ml/minute throughout the procedure and eluate was continuously monitored by absorbance at 254 nm. The protocol for the FPLC run was as follows:

1. The column was equilibrated with 2.5 column volumes of column buffer.
2. The pump was stopped and 160 μl adapted linker was slowly loaded to the column with 1 ml syringe.
3. 200 μl column buffer was used to chase the dead volume of the syringe and adapter into the column.
4. The pump was re-started and fifty 500 μl fractions were collected.
5. Fractions were stored at 4° C. until they were pooled.

E. Pooling Fractions:
1. The trace with optical density of 254 ($OD_{254}$) was used to determine which fractions comprise the initial elution peak (this peak contains the topoisomerase-linker).
2. The best of the fractions in the initial peak were pooled until the total volume was at least 1800 μl. If fractions were eluted in ~500 μl volume, at least the 4 gel-filtration fractions with the highest $OD_{254}$ reading were pooled.
3. Pooled fractions were stored at 4° C. until dilution with storage buffer (see below).

Material eluted from the column in three distinct peaks, as indicated by the $OD_{254}$ results. Column fractions were analyzed by PAGE and silver staining, revealing a strong band in fractions representing a complex comprised of one topoisomerase molecule covalently attached to the topoisomerase-linker DNA (as shown in FIG. 1B).

The FPLC fractions were also assayed for their ability to alter migration of a Taq-generated PCR product. A 300 bp PCR product was incubated with material from fraction 26 and fraction 46 (from the first and second elution peaks, respectively). Reaction mixtures contained the components indicated in Table 1 below in addition to 2 μl 10×T/A PCR buffer (Invitrogen) and $dH_2O$ to 20 μl final volume. After 20 min incubation at 37° C., proteinase K was added to the appropriate tubes and all reactions were incubated an additional 20 min at 37° C. Reactions were loaded directly into a 4% E-gel. The results of these tests showed that migration of the PCR product was retarded after incubation with material from fraction 26, but retardation did not occur with fraction 46. The change in migration was due to a covalent DNA addition to the 300 bp PCR product because the larger species was resistant to proteinase K. These results indicate that the topoisomerase-adapted DNA (topoisomerase-linker) found in fractions 24–31 can covalently attach to DNA that contains a 5'-hydroxyl end with a single A-base 3' overhang.

TABLE 1

| Reaction # | Fraction | 300 bp PCR product (10 ng/μl) | Proteinase K (5 mg/ml) |
|---|---|---|---|
| 1 | #26-13 μl | 4 μl | 1 μl |
| 2 | #26-13 μl | — | 1 μl |
| 3 | #46-13 μl | 4 μl | 1 μl |
| 4 | #46-13 μl | — | 1 μl |
| 5 | — | 4 μl | — |
| 6 | #26-13 μl | — | — |
| 7 | #46-13 μl | — | — |
| 8 | 3 μl Invitrogen 20 bp ladder | | |
| 9 | 3 μl Invitrogen 100 bp ladder | | |

F. QC Protocol:
QC consists of two 10% acrylamide gels and one functional assay (Linker-mediated amplification DNA produced by specific primer extension of Lambda DNA).

The acrylamide gels enable one to assess: 1) the amount of the topoisomerase-adapted oligonucleotide linker contained in the peak fractions (so that dilution factor can be determined), 2) the efficiency of the adaptation step, and 3) the ability of the linker to join to DNA ends created by Taq polymerase.

The functional assay was designed to demonstrate that the Linker in shipping buffer will enable Linker-mediated amplification DNA produced by specific primer extension of Lambda DNA.

1. QC-Gel One

Gel one enabled determination of a dilution factor for the purified topoisomerase-adapted oligonucleotide linker.

The pooled fractions contained a mixture of Topo-adapted and non-adapted DNA. In this experiment, the Topo-adapted DNA runs at 80 bp while the non-adapted (uncut) DNA runs at ~100 bp. The Gel facilitates estimation of the concentration of cut DNA in the pooled fractions, thus determining the appropriate dilution factor for aliquotting. Reactions utilizing the various combinations of parameters shown in Table 2 below were prepared using a 10% TBE acrylamide gel (Novex) according to the manufacturer's instructions.

Briefly, the following procedure was followed:

1. Reagents were combined in the order of dH$_2$O, proteinase K (if used), then sample and incubated 30 minutes at 37° C. Then the 6× DNA loading dye was loaded onto the gel.
2. Samples were loaded onto the 10% TBE acrylamide gel and run until the blue dye (faster migrating of the two dyes reached the bottom of the gel.
3. The gel was opened and stained with ethidium bromide (30 min in mixture of 100 ml dH$_2$O+100 µl 500 µg/ml ethidium bromide stain).
4. The gel was washed for 5 min in 100 ml dH$_2$O to remove the stain.

The gel was photographed using a UV light box.

TABLE 2

| reaction lane | sample (µl) | 5 mg/ml ProteinaseK (µl) | dH$_2$O | 6 × DNA loading dye | DNA concentration in lane | dilution factor for linker |
|---|---|---|---|---|---|---|
| 1 | 1 µl Invitrogen 20 bp ladder | 0 | 18 | 4 | | |
| 2 | 19 µl pooled fractions | 0 | 0 | 4 | | |
| 3 | 19 µl pooled fractions | 1 µl | 0 | 4 | | |
| 4 | 1 µl 5 µg/µl annealed linker oligos | 0 | 19 | 4 | 0.208 | scrap prep |
| 5 | 2 µl 5 µg/µl annealed linker oligos | 0 | 17 | 4 | 0.416 | 5-fold |
| 6 | 3 µl 5 µg/µl annealed linker oligos | 0 | 16 | 4 | 0.625 | 7.5-fold |
| 7 | 19 µl pooled fractions | 1 | 0 | 4 | | |
| 8 | 4 µl 5 µg/µl annealed linker oligos | 0 | 15 | 4 | 0.833 | 10-fold |
| 9 | 5 µl 5 µg/µl annealed linker oligos | 0 | 14 | 4 | 1.04 | 12.5-fold |
| 10 | 6 µl 5 µg/µl annealed linker oligos | 0 | 13 | 4 | 1.25 | 15-fold |

2. Interpretation of Gel I

If blue dye ran to the bottom of the gel, the 20 bp band of the ladder will have run off and the bottom band will be the 40 bp sized fraction). Lane 2 was loaded with a mixture of topoisomerase-adapted linker and non-adapted DNA. Topoisomerase is covalently attached to the adapted DNA, which prevents this DNA from running into the gel. The non-adapted DNA will run as ~100 base pair DNA. Lanes 3 and 7 were loaded with identically prepared samples and should look the same. Sample in these lanes was treated with Proteinase K to allow the topoisomerase-adapted DNA to run into the gel. Thus, lanes 3 and 7 should have an ~80 base pair band (from the topoisomerase-adapted DNA) that is not (or barely) seen in lane 2. Lanes 4, 5, 6, 8, 9 and 10 were "standard lanes" and were loaded with increasing amounts of 100 bp DNA. Visual inspection was used to estimate which of the standard lanes contained roughly the same amount of DNA as is in the lower band (~80 bp) in lanes 3 and 7. The results in Table 2 above (columns 6 and 7) are then used to estimate the concentration of the adapted linker and to then determine the dilution factor.

3. QC-Gel Two

A second gel was run to show that the pooled peak fractions will join to a 400 bp PCR product and retard its migration. For this test reactions utilizing the various combinations of parameters shown in Table 3 below were prepared according to the following procedure:

1. Water, PCR buffer, PCR product diluted to 20 ng/µl in TE, and test sample was to an appropriately labeled Eppendorf tube, mixed and allowed to incubate 30 min at 37° C.
2. Proteinase K was added to the tube, mixed, and allowed to incubate 30 min at 37° C.
3. Samples were loaded on 10% TBE acrylamide gel (Novex) and run until Blue dye (faster migrating dye) reached the bottom of the gel.
4. The gel was opened and stained with ethidium bromide (30 min in mixture of 100 mls dH$_2$O+100 µl 500 µg/ml ethidium bromide stain).
5. The gel was washed for 5 min in 100 mls. dH$_2$O to remove the stain, and
6. The gel was photographed using a UV lightbox.

TABLE 3

| reaction/ lane | test sample | 10 × T/A PCR buffer | 20 ng/µl 400 bp LacZ PCR product | mg/ml ProteinaseK | dH2O (µl) | 6 × DNA loading Dye |
|---|---|---|---|---|---|---|
| 1 | 2 µl 100 bp Invitrogen ladder | 2 | 0 | 0 | 16 | 4 |
| 2 | 0 | 2 | 2 µl | 1 µl | 17 | 4 |
| 3 | 16 µl pooled fractions | 2 | 2 µl | 1 µl | 0 | 4 |

TABLE 3-continued

| reaction/ lane | test sample | 10 × T/A PCR buffer | 20 ng/μl 400 bp LacZ PCR product | mg/ml ProteinaseK | dH2O (μl) | 6 × DNA loading Dye |
|---|---|---|---|---|---|---|
| 4 | 8 μl pooled fractions | 2 | 2 μl | 1 μl | 8 | 4 |
| 5 | 4 μl pooled fractions | 2 | 2 | 1 μl | 12 | 4 |
| 6 | 2 μl pooled fractions | 2 | 2 | 1 μl | 14 | 4 |

4. Interpretation of QC Gel Two

Gel Two should show that topoisomerase-linker causes PCR product to migrate more slowly in a concentration-dependent fashion. If QC Gel Two demonstrates that Linker does attach to PCR product and slows migration in a concentration-dependent fashion, proceed to Dilution of topoisomerase-linker as described below.

G. Dilution of Topoisomerase-linker:

An appropriate dilution factor was determined using Table 4 below, which shows reagent volumes for various possible dilutions. It is assumed that 1500 μl of pooled fraction will be diluted (i.e., a 5-fold dilution will result in 7500 μl linker in buffer, while a 10-fold dilution will result in 15,000 μl linker in buffer). The buffer compositions used were as follows:

2×final wash: 60 mM Tris-Cl pH 7.4, 1 mM EDTA, 4 mM DTT, 0.2 mg/ml BSA and a few grains of phenol red.
Glycerol mix: 90% glycerol, 5 mM Tris-Cl pH 7.5, 0.1% Triton-X-100.

TABLE 4

| Dilution factor | μl pooled fractions | 2 × final wash (μl) | Glycerol mix μl) | TE (μl) | Total final volume (μl) |
|---|---|---|---|---|---|
| 5 | 1500 | 1875 | 3750 | 375 | 7500 |
| 7.5 | 1500 | 2812.5 | 5625 | 1312.5 | 11,250 |
| 10 | 1500 | 3750 | 7500 | 2250 | 15,000 |
| 12.5 | 1500 | 4687.5 | 9375 | 3187.5 | 18,750 |
| 15 | 1500 | 5625 | 11250 | 4125 | 22,500 |

Using the above dilution table (Table 4), the final composition of the buffer for storing topoisomerase-linker is 45% Glycerol, 40 mM NaCl, 0.5 mM EDTA, 0.05% TRITON-X-100 detergent, 20 mM Tris-Cl pH 7.49, 0.05% BSA, 1 mM DTT, and a few grains of phenol red.

EXAMPLE 2

This assay demonstrates that the diluted topoisomerase-linker joins to the A-overhang produced by a sequence-specific Taq-mediated primer extension of PstI-digested Lambda DNA.

A. Sequence-specific Primer Extension of PstI-cut Lambda DNA

1. Preparation of a Polynucleotide Segment from a Vector Clone

A Lambda vector containing a DNA insert was cut to completion with PstI and the cut DNA fragment was dephosphorylated using the following reaction mixture:

2 μg PstI-cut Lambda DNA (Sigma)
5 μl (5 units) calf intestinal phosphatase (CIP)(Roche)
5 μl 10×dephosphorylation buffer (Roche)
dH₂O to 50 μl The reaction mixture was incubated 1 h at 37° C. to obtain a dephosphorylated fragment containing insert DNA of unknown sequence 2. The PstI Cut Dephosphorylated Fragment was Extracted with Phenol and Precipitated as Follows:

1. Add 50 μl dH₂O
2. Add 50 μl phenol (Sigma) and vortex at full power for 10 seconds.
3. Centrifuge at full speed in microfuge (all centrifugation steps are performed at 4° C.) for 1 minute.
4. Remove 90 μl supernatant to fresh Eppendorf flask and to this add 10 III 5M Na-Acetate, 300 μl 100% ethanol, and 2 μl 20 mg/ml glycogen.
5. Vortex at full power for 10 seconds and place on dry ice for 15 minutes.
6. Centrifuge at full speed in microfuge for 15 minutes.
7. Pour off supernatant, add 500 μl 80% ethanol, mix by inverting several times, and centrifuge at full speed in microfuge for 15 minutes.
8. Pour off supernatant, carefully remove last traces of ethanol with 200 μl pipettor (be sure to leave pellet undisturbed—it is better to leave 20 μl ethanol behind than to disturb the pellet).
9. Dry pellet in speed-vacuum, then resuspend in 36 μl dH₂O to obtain a product having a DNA concentration will be 50 ng/pl.

3. Primer Extension was Performed Using PCR

Two μl (100 ng) resuspended DNA was combined with 2 μl 10×T/A PCR buffer (Invitrogen), 1 μl dNTP mixture (each base is at 2.5 mM in mixture), 50 ng primer 3512, 0.4 units Taq polymerase (Sigma), and sufficient dH₂O to obtain 20 μl of the mixture. Primer extension was then carried out using sequence-specific primer 3512 in a thermocycler according to the following profile: 4 min at 94° C., 1 min at 50° C., 20 min at 72° C., 10 min at 4° C. Primer 3512 (5'-AACTCCGTGCAGCCGTACTG) (SEQ ID NO: 13) anneals at base 8565 in Lambda DNA so that the extension would run until the PstI site at bp 9615, where the Taq polymerase produced a single A-base 3' overhang. The extension reaction mixture was stored at −20° C. until used in the linking reaction (step 4 below).

4. Attachment of Topoisomerase-linker to PCR Product (Extended Lambda DNA)

The linking reaction mixture contained 1 μl of topoisomerase-linker prepared as described in Example 1 above, 1 μl of extended Lambda DNA (see Section 3 above), 1 μl 10×T/A PCR buffer (Invitrogen), and 7 μl dH₂O. The reaction mixture was incubated 30 min at 37° C., then stored at −20° C. until used as template for the linker-specific amplification reaction (see Section 5 directly below). The topoisomerase-linker in this reaction has been diluted to final shipping composition.

5. Topoisomerase Linker-specific PCR Amplification

Linker-specific PCR amplification was performed utilizing the following primers:

Primer 2966
5'-GCACTGGAGAAGCATGACACCGGG-3' (SEQ ID NO:14), and

LinkAmp4
5'-TAGAAGGCACAGTCGAGGACTTATCCTA-3' (SEQ ID NO: 11).

Primer 2966 anneals at base 8588 in lambda DNA, and primer LinkAmp4 anneals to the 5' region of the double stranded oligonucleotide topoisomerase linker that has been adapted by covalent attachment of Topoisomerase I (prepared as described above).

The PCR reaction was set up on ice as follows: 1 μl of linking reaction mixture as prepared in Section 4 above, 50 ng primer 2966, 50 ng primer LinkAmp4, 1 µl 10 mM dNTP mixture (mixture contains 2.5 mM each dNTP), 2 µl 10×T/A PCR buffer (Invitrogen), 2 units Taq polymerase (Sigma), and dH₂O to 20 µl. Then the reaction mixture was cycled in a MJ research thermocycler according to the following conditions: After a denaturing step of 4 min at 94° C., cycle 25 times (30" at 94° C., 30" at 60° C., 1 min at 72° C.), followed by 4 min at 72° C. The product of the PCR reaction was stored at −20° C. until used for agarose gel electrophoresis.

6. Analysis

For analysis, 10 µl of the PCR product was run on 2% electrophoresis-gel alongside 4 µl Invitrogen mixed DNA ladder (100 bp and 1000 bp mixture). The presence of 1 kb product indicated the topoisomerase-adapted linker was functional.

EXAMPLE 3

A. BAC DNA Primer Extension:

The bacterial artificial chromosome used here is BAC 327L24. This artificial chromosome vector contains a 170 kb human DNA insert cloned into the EcoRI site of the pBAC3.6e backbone. DNA digestion cocktail: 1.7 µg DNA, 40 units PstI (NEB), 4 µl NEB restriction buffer 3, dH₂O to 40 µl final volume. This mixture was incubated at 37° C. for 2 hr and then the enzyme was heat inactivated by 20 min incubation at 80° C. Subsequently, 4 µl calf intestine phosphatase (CIP) (Roche), 6 µl 10×phosphatase buffer (Roche), and 50 µl dH₂O were added and the mixture was incubated 1 hr at 37° C., then phenol extracted, precipitated, washed with 80% ethanol, dried, and resuspended to a concentration of 40 ng/µl (assuming complete DNA recovery).

120 ng of this cut and dephosphorylated DNA was used as template in a primer extension reaction performed as described above for Lambda DNA except that primer sequence-specific to the bacterial artificial chromosome vector were used instead of the Lambda-specific primer. Primer bac3.6F3 (5'-TCTGTCCTTTTACAGCCAGTAGTG-3'; SEQ ID NO: 15) anneals to the pBac3.6e vector backbone and extends from bp 9597 (numbered as if the BAC-backbone does not contain an insert) to PstI site at bp 8536. Primer bac3.6F2 (5'-AGCGAGGAAGCACCAGGGAACA-3'; SEQ ID NO: 16) extends from bp 9536, and primer bac3.6F4 (5'-TTATATATTCTGCTTACACACGAT-3'; SEQ ID NO: 17) anneals just downstream of primer bac3.6F2.

B. Addition of Topoisomerase-linker to Taq-extended Lambda or BAC Clone DNA:

Linking reaction mixture contained 1 µl of topoisomerase-linker (prepared as described in Example 1 above), 1 µl of the extended BAC DNA (see above), 1 µl 10×T/A PCR buffer (Invitrogen, San Diego, Calif.), and 7 µl dH₂O. Reactions were incubated 30 min at 37° C., then stored at −20° C. until used as templates for topoisomerase-adapted linker-mediated amplification reactions (see directly below).

C. Topoisomerase Linker-specific Primers Used for Topoisomerase Linker-mediated Amplification:

LinkAmp4 (5'-AGGCACAGTCGAGGACTTATCCTA-3'; SEQ ID NO: 18) anneals to the 5' region of the invention topoisomerase-linker prepared as described in Example 1 above, and is used for the initial amplification. It does not produce a product in single-primer PCR reactions using BAC DNA as a template. LinkAmp5 (5'-GCCTCTGAATACTTTCAACAAGTTA-3'; SEQ ID NO: 19) anneals to the 3' region of the topoisomerase-linker and is used for a second, nested amplification (moving (i.e. "walking" closer to the target section of the DNA) and as a sequencing primer (See FIGS. 1A and 1B).

D. Topoisomerase Activity Assay:

Vaccinia Topoisomerase I nicks and relaxes supercoiled DNA. To assay for topoisomerase activity of the invention topoisomerase-adapted linker, supercoiled DNA was incubated with the sample of interest and then the mixture was subjected to agarose gel electrophoresis to determine whether the DNA migrated as supercoiled or relaxed DNA. The assay components do not include DNA containing 5'-hydroxyl ends with single A-base 3' overhangs. Because the assay does not include a substrate for the topoisomerase-linker, topoisomerase that is covalently attached to Linker DNA remains attached to the Linker. Thus, the assay detects only free topoisomerase. This assay shows that the mixture loaded on the column contains free topoisomerase activity, but the pooled peak topoisomerase-linker fractions do not. This indicates that the column effectively separates free topoisomerase from the covalent DNA/topoisomerase complex. Thus, the assay detects free topoisomerase, not enzyme that is covalently attached to the duplex linker construct.

E. Purification and Sequencing of PCR Products:

PCR products were electrophoresed through 1% agarose gels run in 1 x TAE buffer. Desired products were excised with a razor blade and removed from the agarose plugs by three different protocols. 1) SpinClean gel purification: Excised plugs were frozen, placed in a SNAP mini-prep column, and centrifuged at full-speed in a microfuge for 2 min. 50 µl dH₂O was then added to the column and a second 2 min spin was performed. The total volume eluted was ~150 µl and the agarose was entirely retained on the column frit. 2) SpinClean-precipitation purification: 100 µl of the SpinClean gel purification eluate was precipitated by addition of 10 µl 3 M Na-acetate and 300 µl 100% ethanol, followed by 15 min incubation on dry ice and then 15 min centrifugation at 4° C. The pellet was then washed with 80% ethanol, dried, and resuspended in 40 µl dH₂O. 3) Na-Iodide-SNAP purification: Performed according to protocol in XL-PCR kit (Invitrogen, San Diego, Calif.), in which each PCR product is ultimately eluted in 40 µl dH₂O.

Sequencing reactions for DNAs purified by the SpinClean gel purification method or SpinClean precipitation method contained 19 µl DNA and 1 µl (7 ng) LinkAmp5 oligo. Sequencing reactions for DNAs purified by the Na-iodide SNAP gel purification method contained 9 µl DNA, 10 µl dH₂O, and 1 µl (7 ng) LinkAmp5 oligo as a sequencing primer.

EXAMPLE 4

A. Kinase Improves Efficiency of Adaptation of the Linker Duplex by Topoisomerase:

Vaccinia Topoisomerase I binds to duplex DNA and cleaves the phosphodiester backbone of one strand after a 5'-CCCTT in the scissile strand. The phospho-tyrosyl bond between the DNA and enzyme can subsequently be attacked by the 5' hydroxyl of the original cleaved strand, thus reversing the reaction and releasing the topoisomerase. Because topoisomerase catalyzes both cleavage and religation, the structures in FIGS. 1A and 1B will reach an equilibrium. Phosphorylation of the 5' end of the leaving group should therefore drive the reaction towards the cleaved product, increasing the efficiency of preparation of the topoisomerase-adapted linker.

This hypothesis was tested by comparing the cleavage products obtained after annealed oligos were incubated with Topoisomerase I in the presence or absence of T4 polynucleotide kinase (PNK). A duplex linker oligonucleotide was prepared by annealing T7 top (5'-GACTCGTAAATACGACTCACTATAGG-TATCCGTGTCGCCCTTATTCCGA TAGTGAC-3'; SEQ ID NO: 20) to a 5'-phosphorylated T7 bottom (5'-AGGGCGACACGGATACCTATAGTGAGT-GAGTCGTATTACGAG TCTAG-3'; SEQ ID NO: 21), and Topo5 (SEQ ID NO: 1) at a molar ratio of 1:1:5, respectively, in a mixture containing 70 mM Tris-HCl pH 7.6, 10 mM MgCl$_2$, mM DTT, 200 mM NaCl. Topoisomerase adaptation reactions were set up with or without 20 units PNK as follows: 5 µl (600 ng) annealed oligos, 70 mM Tris-HCl pH 7.6, 10 mM MgCl$_2$, 5 mM DTT, 5 mM ATP, 2 µg Vaccinia Topoisomerase, dH$_2$O to final volume of 20 µl. Each reaction was incubated 30 min at 37° C., then split into two 10 µl aliquots. One aliquot from each adaptation was then treated with 2 µl 5 mg/ml proteinase K for 30 min at 37° C. Samples were loaded onto a 15% TBE/urea gel (Novex) as follows: Lanes: 1) 300 ng annealed oligos; 2) 1 µg T7-top oligo alone; 3) 1 µg T7 bottom oligo alone; 4) Topo-adaptation reaction with PNK and treated with proteinase K before loading (100 ng DNA); 5) Topo-adaptation reaction with PNK, without proteinase K treatment (100 ng DNA); 6) Topo-adaptation reaction without PNK, with proteinase K (100 ng DNA); 7) Topo-adaptation reaction without PNK and without proteinase K treatment (100 ng DNA).

The results of these tests show that addition of PNK increases accumulation of the cleaved product in lines 4 and 6. Although the oligos used to illustrate this principle are not those used for preparation of the preferred topoisomerase-adapted linker, similar results were obtained using the oligo used in preparation of the preferred topoisomerase-adapted linker. Therefore, PNK was used in all subsequent adaptations of the topoisomerase linker by covalent attachment of Topoisomerase I.

However, Topoisomerase I is a DNA binding protein as well as a protein that covalently attaches to DNA. The results of the above tests also illustrate that DNA samples must be treated with proteinase K before electrophoresis to allow the DNA to migrate correctly during agarose-gel electrophoresis.

Fractions were further characterized by assaying for DNA unwinding (Topoisomerase) activity. Because the assay does not include a substrate for the topoisomerase-linker, topoisomerase that is covalently attached to Linker DNA remains attached to the linker. Thus, the assay detects only free topoisomerase. The Sephacryl S-200 chromatography should also separate the covalent DNA/topoisomerase complex from PNK (Topoisomerase I and PNK have similar molecular masses –33 kd vs. 30 kd, respectively). Kinase activity in the fractions could not be tested because the column load contained a great deal of ATP that would compete with the radioactive ATP used in standard kinase assays. However, a similar S-200 sephacryl column was loaded with kinase and DNA (and no ATP) and FPLC fractionation was performed. When fractions were assayed for kinase activity, it was shown that the fractions 24–31 corresponding to about 12 through 14 ml collected, free of kinase activity (data not shown). This result suggests that the FPLC gel-purification will separate the covalent Topoisomerase I/DNA complex from PNK.

B. Topoisomerase-linker Enables Linker-mediated Amplification (LMA) of a Taq-mediated Primer Extension Product:

In order to develop topoisomerase-linkers as a tool to facilitate PCR amplification of DNA fragments for which the sequence of only one end is known, it was necessary to demonstrate that the topoisomerase-linker will attach to the product of a Taq-mediated primer extension, and that the attached DNA will serve as a primer-binding site for a subsequent PCR. When invention topoisomerase-linker was incubated with PCR extension products obtained using primers specific to known sequences of 50 kb Lambda phage DNA and 170 kb BAC DNA to obtain a template suitable for topoisomerase linker-mediated amplification, the templates were efficiently amplified using one Linker-specific primer and one primer fully complementary to a second, internal primer binding site on the extension product from the first round of PCR amplification. A contaminating band at ~400 bp in lanes 1 and 2 of the gel was not present when a different template-specific primer is used (lanes 3 and 4), indicating that results of an initial PCR can be influenced by primer design.

A second round of nested Taq-mediated PCR amplification was performed using as template the extension product from the first round of PCR amplification. For nested PCR a nested set of linker-specific and sequence-specific primers that are internal to those used in the first PCR extension were used to selectively amplify a shorter segment containing unknown sequence using the initial PCR products as a template. For nested PCR amplification, unpurified product from the reactions in lanes 1 and 2 was diluted 1/1000, amplified using nested primers, and the product was loaded in lanes 7 and 8, respectively. The nested PCR gave a robust product free of the 400 bp contaminating band. Subsequent sequence analysis confirmed the identity of the amplified DNA. Thus, the invention topoisomerase-linkers can be used to isolate DNA of unknown sequence and length and nested PCR can be used to confirm the identity of isolated amplification products so obtained.

C. PCR Products Generated by Linker-mediated Amplification can be Sequenced Directly:

The PCR products obtained as described above were purified from agarose by the SpinClean gel purification method. Good quality sequence was obtained from 9 templates of about 500 bp in length purified by the SpinClean gel purification method, while none of the SpinClean precipitation DNAs gave any sequence. It is likely that the poor results with the precipitation method were the result of DNA loss during the precipitation.

In order to compare SpinClean gel purification /SpinClean precipitation sequencing results with Na-iodide SNAP gel purification results, the same 9 templates were-reamplified and the products purified according to the Na-iodide-SNAP gel purification method. These templates gave excellent sequence, with most reads >550 bases. The primer LinkAmp5 was used for all sequencing reactions, demonstrating that it can be used for PCR products generated using either LinkAmp4 or LinkAmp5. Sequencing results are summarized in Table 2 (the number in the "Bases Read" column indicates the base at which the sequence became difficult to call by visual inspection).

D. Conclusion:

The results described above also demonstrate that the topoisomerase-adapted linker covalently attached to an A-tailed PCR product, and the linker enabled PCR amplification of templates generated through gene-specific primer extension of Lambda and BAC DNA. It is also demonstrated that a nested PCR performed with the internal linker-specific primer (LinkAmp5) selectively amplified the desired DNA from the mixture of DNA species contained within an initial Linker-mediated-amplification product. In addition, it is shown that PCR products generated through Linker-mediated-amplification could be purified using SNAP columns and then sequenced directly using the LinkAmp5 primer (Table 1). DNA purified using the Na-iodide-SNAP gel purification method gave the highest quality sequencing results.

While the invention has been described in detail with reference to certain preferred embodiments thereof, it will be understood that modifications and variations are within the spirit and scope of that which is described and claimed.

What is claimed is:

1. An isolated oligonucleotide consisting of a sequence according to SEQ ID NO: 11.

2. An isolated oligonucleotide consisting of a sequence according to SEQ ID NO: 12.

* * * * *

SEQUENCE LISTING

<160> NUMBER OF SEQ ID NOS: 21

<210> SEQ ID NO 1
<211> LENGTH: 16
<212> TYPE: DNA
<213> ORGANISM: ARTIFICIAL
<220> FEATURE:
<223> OTHER INFORMATION: oligonucleotide Topo5

<400> SEQUENCE: 1
caacactatc ggaata                                                    16

<210> SEQ ID NO 2
<211> LENGTH: 72
<212> TYPE: DNA
<213> ORGANISM: ARTIFICIAL
<220> FEATURE:
<223> OTHER INFORMATION: oligonucleotide linktop4bio

<400> SEQUENCE: 2
tagaaggcac agtcgaggac ttatcctagc ctctgaatac tttcaacaag ttacacccctt    60 attccgatag tg                                                        72

<210> SEQ ID NO 3
<211> LENGTH: 72
<212> TYPE: DNA
<213> ORGANISM: ARTIFICIAL
<220> FEATURE:
<223> OTHER INFORMATION: oligonucleotide - linkbot4

<400> SEQUENCE: 3
agggtgtaac ttgttgaaag tattcagagg ctaggataag tcctcgactg tgccttctaa    60
aaaaaaaaaa aa                                                        72

<210> SEQ ID NO 4
<211> LENGTH: 5
<212> TYPE: DNA
<213> ORGANISM: ARTIFICIAL
<220> FEATURE:
<223> OTHER INFORMATION: consensus pentapyrimidine element

<400> SEQUENCE: 4 ycctt                                                                 5

<210> SEQ ID NO 5
<211> LENGTH: 12
<212> TYPE: DNA
<213> ORGANISM: ARTIFICIAL
<220> FEATURE:
<223> OTHER INFORMATION: example of alternative Vaccinia topoisomerase

<400> SEQUENCE: 5
gcccttattc cc                                                        12

<210> SEQ ID NO 6
<211> LENGTH: 12
<212> TYPE: DNA
<213> ORGANISM: ARTIFICIAL
<220> FEATURE:
<223> OTHER INFORMATION: example of alternative Vaccinia topoisomerase

<400> SEQUENCE: 6
tcgcccttat tc                                                        12

<210> SEQ ID NO 7
<211> LENGTH: 12
<212> TYPE: DNA
<213> ORGANISM: ARTIFICIAL
<220> FEATURE:
<223> OTHER INFORMATION: example of alternative Vaccinia topoisomerase

<400> SEQUENCE: 7
tgtcgccctt at                                                          12

<210> SEQ ID NO 8
<211> LENGTH: 12
<212> TYPE: DNA
<213> ORGANISM: ARTIFICIAL
<220> FEATURE:
<223> OTHER INFORMATION: example of alternative Vaccinia topoisomerase

<400> SEQUENCE: 8
gtgtcgccct ta                                                          12

<210> SEQ ID NO 9
<211> LENGTH: 53
<212> TYPE: DNA
<213> ORGANISM: ARTIFICIAL
<220> FEATURE:
<223> OTHER INFORMATION: first oligonucleotide in the linker

<400> SEQUENCE: 9
tagaaggcac agtcgaggac ttatcctagc ctctgaatac tttcaacaag tta             53

<210> SEQ ID NO 10
<211> LENGTH: 58
<212> TYPE: DNA
<213> ORGANISM: ARTIFICIAL
<220> FEATURE:
<223> OTHER INFORMATION: second oligonucleotide in the linker

<400> SEQUENCE: 10
agggtgtaac ttgttgaaag tattcagagg ctaggataag tcctcgactg tgccttct        58

<210> SEQ ID NO 11
<211> LENGTH: 28
<212> TYPE: DNA
<213> ORGANISM: ARTIFICIAL
<220> FEATURE:
<223> OTHER INFORMATION: oligonucleotide that anneals to the 5' end of
      the second oligonuc leotide in the linke

<400> SEQUENCE: 11
tagaaggcac agtcgaggac ttatccta                                         28

<210> SEQ ID NO 12
<211> LENGTH: 25
<212> TYPE: DNA
<213> ORGANISM: ARTIFICIAL
<220> FEATURE:
<223> OTHER INFORMATION: oligonucleotide that anneals to the area 3' of
      the target site

<400> SEQUENCE: 12
gcctctgaat actttcaaca agtta                                            25

<210> SEQ ID NO 13
<211> LENGTH: 20
<212> TYPE: DNA

```
<213> ORGANISM: ARTIFICIAL
<220> FEATURE:
<223> OTHER INFORMATION: primer 3512 anneals at base 8565 in Lambda DNA

<400> SEQUENCE: 13
aactccgtgc agccgtactg                                               20

<210> SEQ ID NO 14
<211> LENGTH: 24
<212> TYPE: DNA
<213> ORGANISM: ARTIFICIAL
<220> FEATURE:
<223> OTHER INFORMATION: linker-specific PCR amplification

<400> SEQUENCE: 14
gcactggaga agcatgacac cggg                                          24

<210> SEQ ID NO 15
<211> LENGTH: 24
<212> TYPE: DNA
<213> ORGANISM: ARTIFICIAL
<220> FEATURE:
<223> OTHER INFORMATION: primer bac3.6F3

<400> SEQUENCE: 15 tctgtcccttt tacagccagt agtg                                         24

<210> SEQ ID NO 16
<211> LENGTH: 22
<212> TYPE: DNA
<213> ORGANISM: ARTIFICIAL
<220> FEATURE:
<223> OTHER INFORMATION: primer bac3.6F2

<400> SEQUENCE: 16
agcgaggaag caccagggaa ca                                            22

<210> SEQ ID NO 17
<211> LENGTH: 24
<212> TYPE: DNA
<213> ORGANISM: ARTIFICIAL
<220> FEATURE:
<223> OTHER INFORMATION: primer bac3.6F4

<400> SEQUENCE: 17
ttatatattc tgcttacaca cgat                                          24

<210> SEQ ID NO 18
<211> LENGTH: 24
<212> TYPE: DNA
<213> ORGANISM: ARTIFICIAL
<220> FEATURE:
<223> OTHER INFORMATION: primer LinkAmp4

<400> SEQUENCE: 18
aggcacagtc gaggacttat ccta                                          24

<210> SEQ ID NO 19
<211> LENGTH: 25
<212> TYPE: DNA
<213> ORGANISM: ARTIFICIAL
<220> FEATURE:
<223> OTHER INFORMATION: primer LinkAmp5

<400> SEQUENCE: 19
gcctctgaat actttcaaca agtta                                         25
```

-continued

```
<210> SEQ ID NO 20
<211> LENGTH: 56
<212> TYPE: DNA
<213> ORGANISM: ARTIFICIAL
<220> FEATURE:
<223> OTHER INFORMATION: oligonucleotide, part of topoisomerase
      adaptation reactions

<400> SEQUENCE: 20
gactcgtaaa tacgactcac tataggtatc cgtgtcgccc ttattccgat agtgac          56

<210> SEQ ID NO 21
<211> LENGTH: 47
<212> TYPE: DNA
<213> ORGANISM: ARTIFICIAL
<220> FEATURE:
<223> OTHER INFORMATION: oligonucleotide, part of topoisomerase
      adaptation reactions

<400> SEQUENCE: 21
agggcgacac ggatacctat agtgagtgag tcgtattacg agtctag                   47
```